US011529398B2

(12) United States Patent
Csikos et al.

(10) Patent No.: US 11,529,398 B2
(45) Date of Patent: *Dec. 20, 2022

(54) USE OF BOTULINUM NEUROTOXIN IN THE TREATMENT OF SIALORRHEA

(71) Applicant: Merz Pharma GmbH & Co. KGaA, Frankfurt am Main (DE)

(72) Inventors: Janos Csikos, Frankfurt am Main (DE); Irena Pulte, Eschborn (DE); Michael Althaus, Osten (DE); Markus Krueer, Kelkheim (DE); Nico Wegener, Frankfurt am Main (DE)

(73) Assignee: MERZ PHARMA GMBH & CO. KGAA, Frankfurt Am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,799

(22) Filed: Jun. 5, 2020

(65) Prior Publication Data

US 2020/0297823 A1   Sep. 24, 2020

Related U.S. Application Data

(63) Continuation of application No. 16/129,311, filed on Sep. 12, 2018, now Pat. No. 10,709,772, which is a continuation of application No. PCT/EP2018/056850, filed on Mar. 19, 2018.

(30) Foreign Application Priority Data

Mar. 24, 2017   (EP) .................................... 17162719

(51) Int. Cl.
| A61K 38/48 | (2006.01) |
| A61K 9/00 | (2006.01) |
| A61P 1/00 | (2006.01) |
| A61P 43/00 | (2006.01) |

(52) U.S. Cl.
CPC ........ *A61K 38/4893* (2013.01); *A61K 9/0019* (2013.01); *A61K 9/0053* (2013.01); *A61P 1/00* (2018.01); *A61P 43/00* (2018.01); *Y02A 50/30* (2018.01)

(58) Field of Classification Search
CPC .............. A61K 38/164; A61K 38/4893; C07K 14/33
See application file for complete search history.

(56) References Cited

U.S. PATENT DOCUMENTS

| 7,879,341 | B2 | 2/2011 | Taylor |
| 8,372,645 | B2 | 2/2013 | Taylor |
| 8,398,998 | B2 | 3/2013 | Bigalke et al. |
| 8,652,489 | B2 | 2/2014 | Taylor |
| 9,050,367 | B2 | 6/2015 | Taylor |
| 9,220,783 | B2 | 12/2015 | Taylor |
| 10,105,421 | B2 | 10/2018 | Taylor |
| 10,709,772 | B2 * | 7/2020 | Csikos ................. A61K 9/0053 |
| 2006/0018931 | A1 | 1/2006 | Taylor |
| 2009/0142430 | A1 | 6/2009 | Sanders et al. |
| 2011/0091503 | A1 | 4/2011 | Taylor |
| 2013/0121987 | A1 | 5/2013 | Taylor |
| 2014/0105882 | A1 | 4/2014 | Taylor |
| 2015/0231259 | A1 | 8/2015 | Taylor |
| 2016/0074486 | A1 | 3/2016 | Taylor |
| 2016/0151467 | A1 | 6/2016 | Choi et al. |
| 2016/0202245 | A1 | 7/2016 | Brunn |
| 2017/0340823 | A1 | 11/2017 | Vogt |
| 2018/0360995 | A1 | 12/2018 | Bancel et al. |

FOREIGN PATENT DOCUMENTS

| WO | 2005007185 A2 | 1/2005 |
| WO | 2006020208 A2 | 2/2006 |
| WO | 2009114748 A1 | 9/2009 |
| WO | 2010013494 A1 | 2/2010 |
| WO | 2013049508 A1 | 4/2013 |
| WO | 2014207109 A1 | 12/2014 |

OTHER PUBLICATIONS

Daughton et al. Lower-dose prescribing: Minimizing "side effects" of pharmaceuticals on society and the environment. Science of the Total Environment. 2013, vol. 443, pp. 324-337. (Year: 2013).*
McCormack et al. Is bigger better? An argument for very low starting doses. Canadian Medical Association Journal. Jan. 11, 2011, vol. 183, No. 1, pp. 65-69. (Year: 2011).*
Breheret, R., et al., "Ultrasound-guided botulinum toxin injections for treatment of drooling," European Annals of Otorhinolaryngology, Head and Neck diseases, (2011), vol. 128: 224-229.
Suskind, Dana L., et al., "Clinical Study of Botulinum-A Toxin in the Treatment of Sialorrhea in Children With Cerebral Palsy," Laryngoscope, (2002), vol. 112, No. 01: 73-81.
Castelnovo, Giovanni, et al., "Comparison of different sites of injections of incobotulinumtoxin (XEOMIN®) into the major salivary glands in drooling," Movement Disorders, (2013), vol. 28: Abstract Supplement.
Jongerius, Peter H., et al., "Assessment of Salivary flow Rate: Biologic Variation and Measure Error," The Laryngoscope, (2004), vol. 114,: 1801-1804.
Likert, Rensis, "A Technique for the Measurement of Attitudes," Archives of Psychology, (1932), vol. 22 No. 140: 5-55.
Thomas-Stonell, Nancy, et al., "Three Treatment Approaches and Clinical Factors in the Reduction of Drooling," Dysphagia, (1988), vol. 3: 73-78.
Kalf, Johanna G., et al., "Reproducibility and Validity of Patient-Rated Assessment of Speech, Swallowing, and Saliva Control in Parkinson's Disease," Arch. Phys. Med. Rehabil., (2011), vol. 92: 1152-1158.

(Continued)

*Primary Examiner* — Jeffrey E. Russel
(74) *Attorney, Agent, or Firm* — McBee Moore & Vanik IP, LLC

(57) ABSTRACT

This invention relates to improved uses of botulinum neurotoxins in the treatment of sialorrhea or diseases or conditions relating to increased saliva production. In particular are botulinum neurotoxins disclosed which are administered into parotid and submandibular glands in a dose ratio between 1.45 to 1 and 1.7 to 1.

22 Claims, 5 Drawing Sheets

Specification includes a Sequence Listing.

(56) References Cited

OTHER PUBLICATIONS

Needleman, Saul B., et al., "A General Method Applicable to the Search for Similarities in the Amino Acid Sequence of Two Proteins," J. Mol. Biol., (1970), vol. 48: 443-453.
Smith, Temple F., et al., "Comparison of Biosequences," Advances in Applied Mathematics, (1981), vol. 2: 482-489.
Pearce, L. Bruce, et al., "Measurement of Botulinum Toxin Activity: Evaluation of the Lethality Assay," Toxicology and Applied Pharmacology, (1994), vol. 128: 69-77.
Dressler, Dirk, et al., "Mouse Diaphragm Assay for Detection of Antibodies Against Botulinum Toxin Type B," Movement Disorders, (2005), vol. 20, No. 12: 1617-1619.
Keller, J.E., "Recovery From Botulinum Neurotoxin Poisoning in Vivo," Neuroscience, (2006), pp. 1-9.
Mosseri, Ashley, et al., "Histopathologic Effects of Onabotulinum Toxin A Treatment in Pediatric Submandibular Glands," Otolaryngology—Headh and Neck Surgery, (2016), pp. 1-3.
Fujinaga, Y., et al., "A novel function of botulinum toxin-associated proteins: HA proteins disrupt intestinal epithelial barrier to increase toxin absorption," Toxicon, (2009), vol. 54: 583-586.
Sugawara, Yo, et al., "Botulinum hemagglutinin disrupts the intercellular epithelial barrier by directly binding E-cadherin," Journal of Cell Biology, (2010), vol. 189, No. 4: 691-700.
Lee, Kwangkook, et al., "Molecular basis for disruption of E-cadherin adhesion by botulinum neurotoxin A complex," Science, (2014), vol. 344, No. 6190: 1405-1410.
Davis, Michael A., et al., "Blocked Acinar Development, E-Cadherin Reduction, and Intraepithelial Neoplasia upon Ablation of p120-Catenin in the Mouse Salivary Gland," Developmental Cell, (2006), vol. 10: 21-31.
Baker, Olga J., "Tight Junctions in Salivary Epithelium," Journal of Biomedicine and Biotechnology, (2010), vol. 2010: 1-14.
Xu, H., et al., "Pre- and Post-synaptic Effects of Botulinum Toxin A on Submandibular Glands," Journal of Dental Research, (2015), vol. 94, No. 10: 1-9.
Shan, Xiao-Feng, et al., "Botulinum toxin A inhibits salivary secretion of rabbit submandibular gland," International Journal of Oral Science, (2013), vol. 5: 217-223.
Holsinger, F. Christopher, et al., "Anatomy, Function, and Evaluation of the Salivary Glands," Salivary Gland Disorders, (2007), pp. 1-16.
Howlett, D.C., "High resolution ultrasound assessment of the parotid gland," Br. J. Radiol., (2003), vol. 76, No. 904: 271-277.
Higgins, Desmond G., et al., "Fast and sensitive multiple sequence alignments on a microcomputer," CABIOS Communications, (1989), vol. 5, No. 2: 151-153.
PCT International Search Report for PCT/EP2018/056850, dated May 18, 2018.
Alvarenga, et al., "BOTOX-A injection of salivary glands for drooling," Journal of Pediatric Surgery, (2016), 1531-5037.
Barbero, et al., "Long-term follow-up of ultrasound-guided botulinum toxin-A injections for sialorrhea in neurological dysphagia," Journal of Neurology, (2015), vol. 262, No. 12: 2662-2667.
Ellies, et al., "Successful Management of Drooling with Botulinum Toxin A in Neurologically Disabled Children," Neuropediatrics, (2002), vol. 33, No. 6: 327-330.
Wilken, et al., "Successful Treatment of Drooling in Children with Neurological Disorders with Botulinum Toxin A or B," Neuropediatrics, (2008), vol. 39, No. 4: 200-204.
Wu, et al.m "Botulinum Toxin Type A on Oral Health in Treating Sialorrhea in Children With Cerebral Palsy: A Randomized, Double-Blind, Placebo-Controlled Study," Journal of Child Neurology, (2011), vol. 26, No. 7: 838-843.
Tiigimäe-Saar Janne et al: "Does Botulinum neurotoxin type A treatment for sialorrhea change oral health?", Clinical Oral Investigations, (2017), vol. 21, No. 3: 795-800.
Porta, et al., "Treatment of sialorrhoea with ultrasound guided botulinum toxin type A injection in patients with neurological disorders," Journal of Neurology Neurosurgery and Psychiatry, (2001), vol. 70, No. 4: 538-540.
Narayanaswami, et al., "Drooling in Parkinson's disease: A randomized controlled trial of incobotulinum toxin A and meta-analysis of Botulinum toxins," Parkinsonism And Related Disorders, (2016), vol. 30: 73-77.
Kahl et al. Botulinum toxin as an effective treatment of clozapine-induced hypersalivation. Psychopharmacology. 2004, vol. 173, pp. 229-230. (Year: 2004).
Cardona et al. Effect of Recurrent Onabotulinum Toxin A Injection Into the Salivary Glands: An Ultrasound Measurement. The Laryngoscope. Oct. 2015, vol. 125, E328-E332. (Year: 2015).
Alvarenga et al. BOTOX-A injection of salivary glands for drooling. Journal of Pediatric Surgery. 2017, vol. 52, pp. 1283-1286. Epub = Oct. 14, 2016. (Year: 2016).
Dressler. Routine use of XEOMIN in patients previously treated with BOTOX: long term results. European Journal of Neurology. 2009, vol. 16, Supplement 2, pp. 2-5. (Year: 2009).
Frevert et al. Complexing proteins in botulinum toxin type A drugs: a help or a hindrance? Biologies: Targets & Therapy. 2010, vol. 4, pp. 325-332. (Year: 2010).
S. Bellows & J. Jankovic, "Immunogenicity Associated with Botulinum Toxin Treatment", Toxins (11) 491 (pub. Aug. 26, 2019).
A. Lipp et al., "A randomized trial of botulinum toxin A for treatment of drooling", Neurology 2003 (61): 1279-1281.
E. Moeller et al., "Onabotulinumtoxin A Treatment of Drooling in Children with Cerebral Palsy: A Prospective, Longitudinal Open-Label Study", Toxins (7) 2481-2493 (pub. Jun. 30, 2015).
F. Scaglione, "Conversion Ratio between Botox, Dysport, and Xeomin in Clinical Practice", Toxins 2016 (8) 65 (pub. Mar. 4, 2016).

* cited by examiner

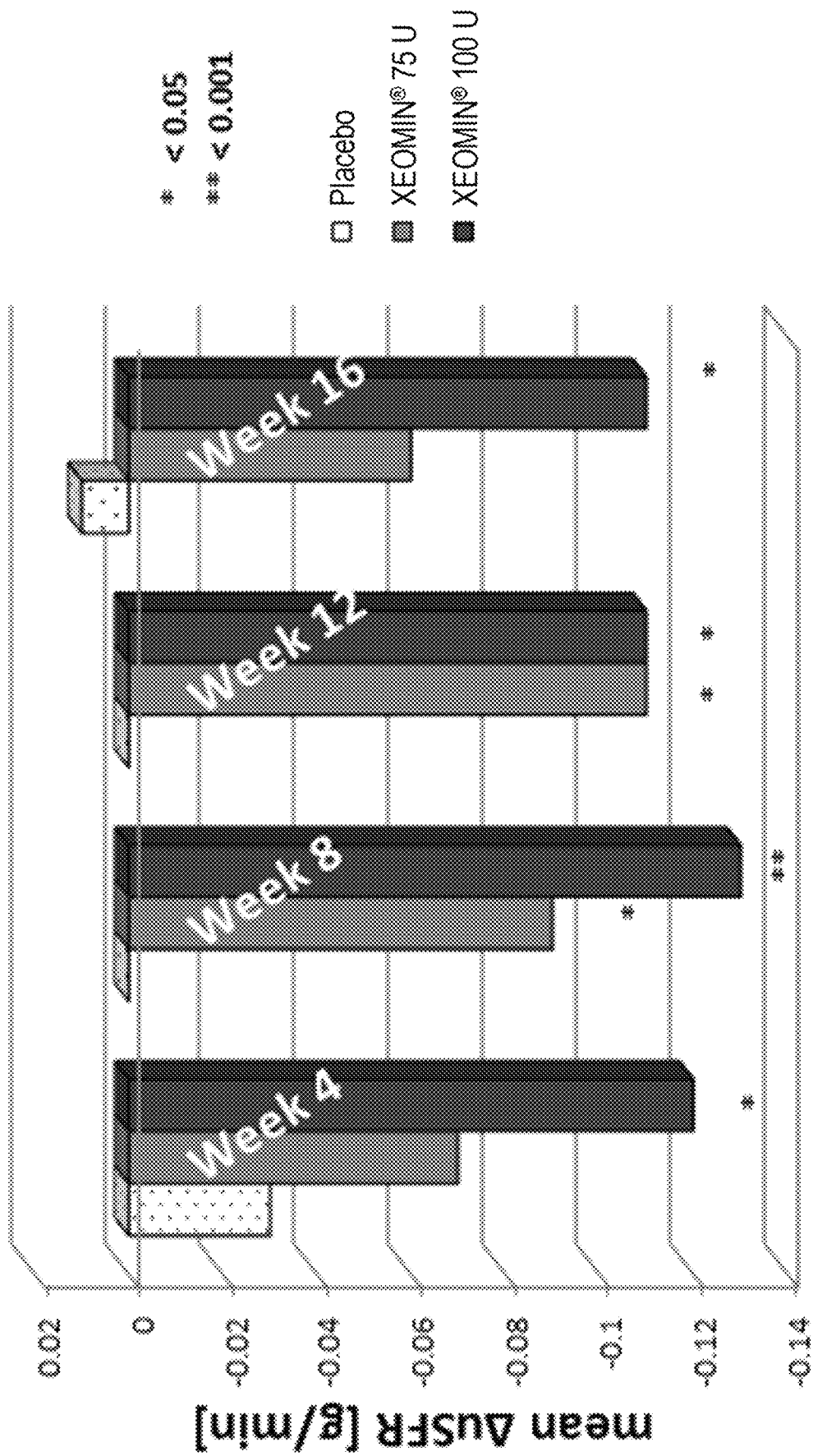
Figure 1: Mean reduction in objectively measured unstimulated Salivary Flow Rate (uSFR) from baseline (FAS)

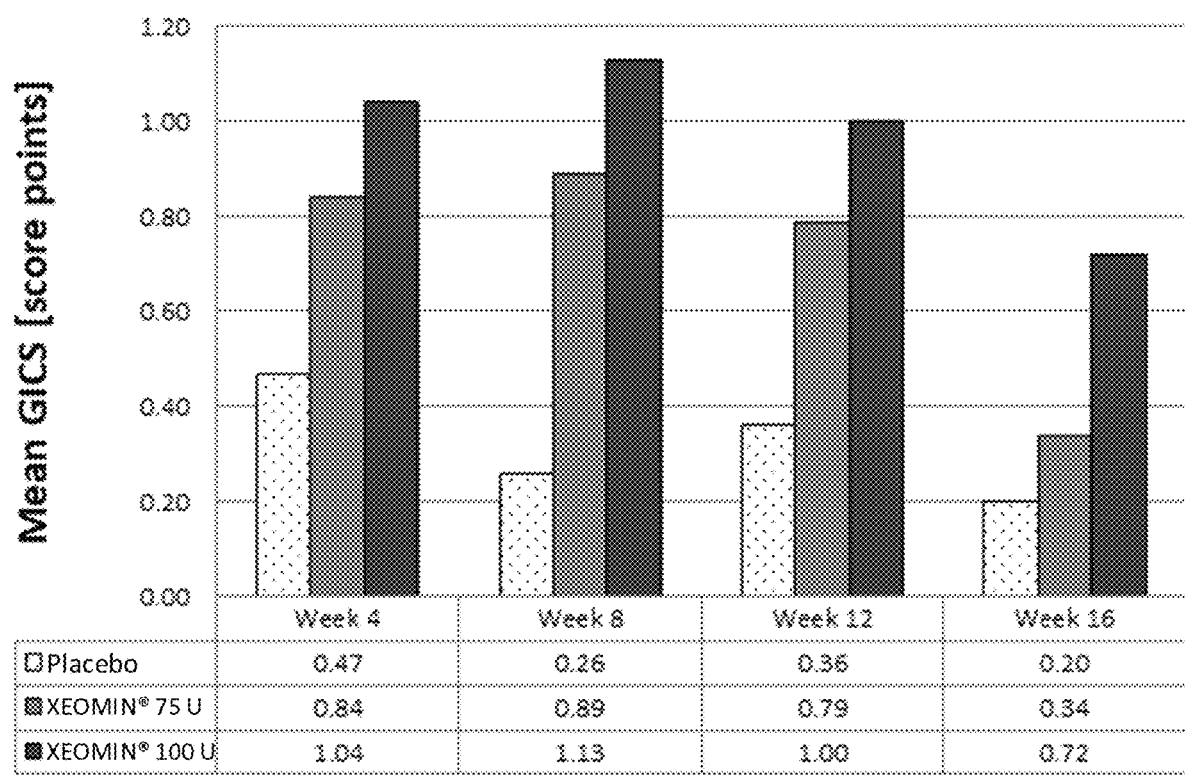
Figure 2: Mean Global Impression of Change Scale (GICS) (FAS)

Figure 3: Response rate in Subject's GICS over time (FAS)
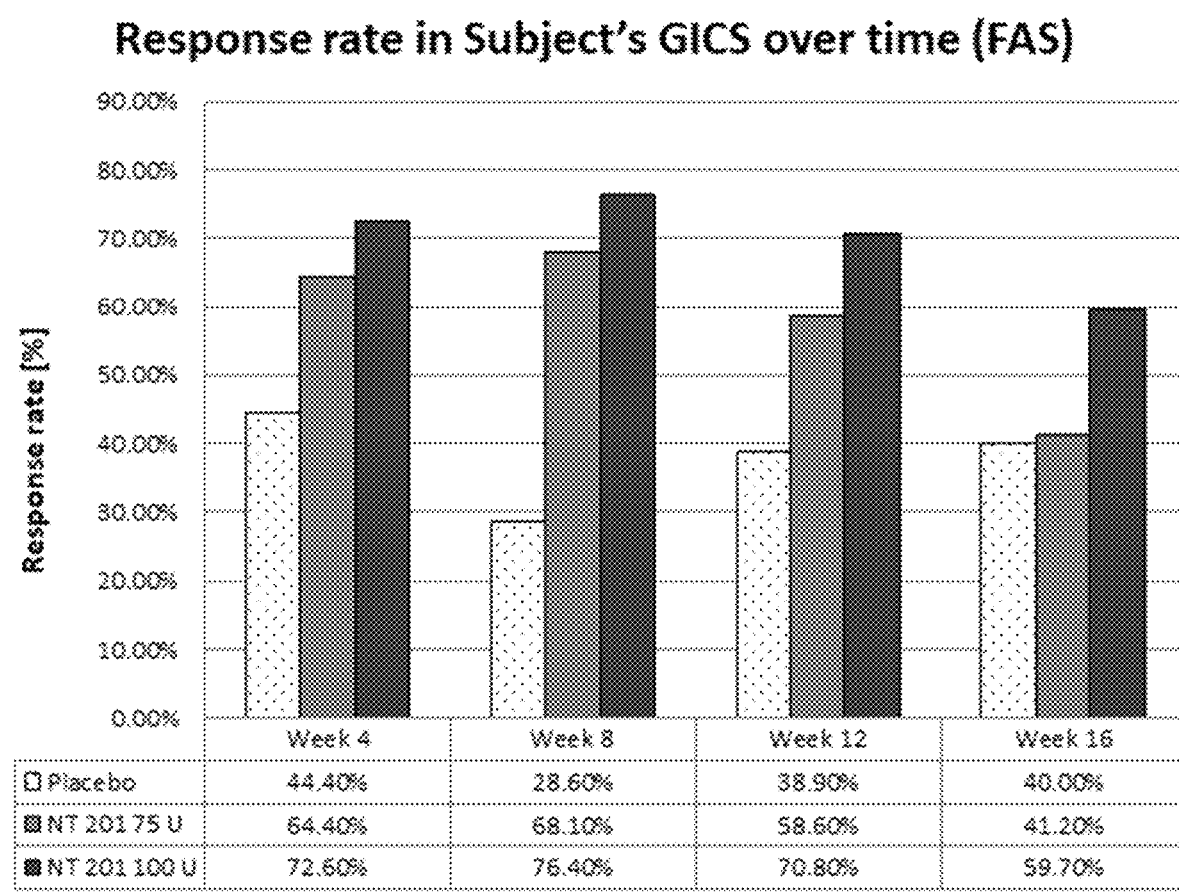

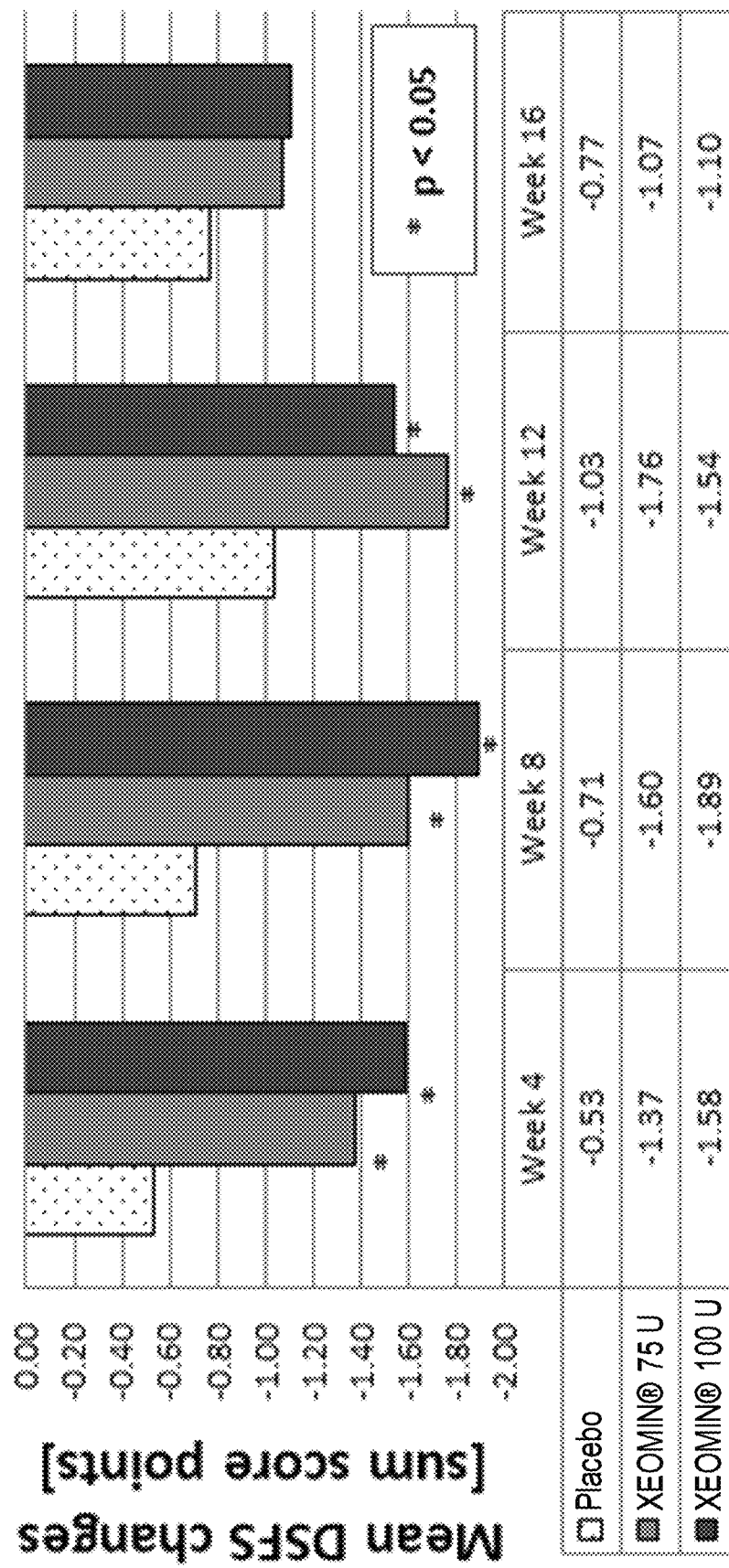
Figure 4: Mean reduction of Drooling Severity and Frequency Sum score (DSFS) from baseline (FAS)

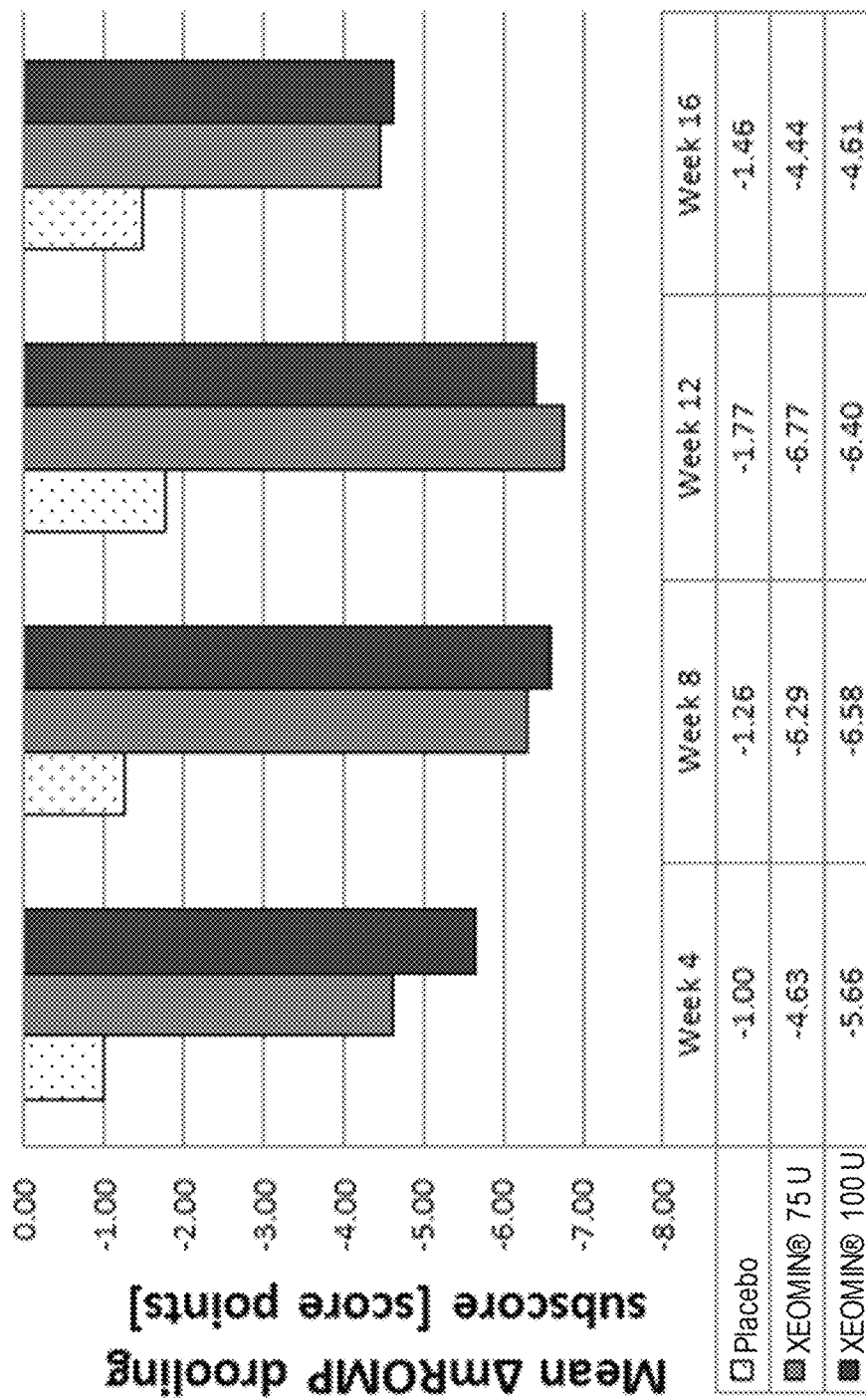
Figure 5: Mean mROMP drooling subscore reduction from baseline (FAS)

SEQUENCE LISTING

```
<160> NUMBER OF SEQ ID NOS: 14

<210> SEQ ID NO 1
<211> LENGTH: 3891
<212> TYPE: DNA
<213> ORGANISM: Clostridium botulinum

<400> SEQUENCE: 1
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttgggtggga     360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta aagtaaatac taatgcctat tatgaaatga gtgggttaga agtaagcttt     780
gaggaactta acatttggg gggacatgat gcaaagttta gatagtttt acaggaaaac     840 gaatttcgtc tatattatta taataagttt aaagatatag caagtacact taataaagct     900
aaatcaatag taggtactac tgcttcatta cagtatatga aaaatgtttt taaagagaaa     960
tatctcctat ctgaagatac atctggaaaa ttttcggtag ataaattaaa atttgataag    1020
ttatacaaaa tgttaacaga gatttacaca gaggataatt tgttaagtt ttttaaagta    1080 cttaacagaa aaacatattt gaatttttgat aaagccgtat taagataaa tatagtacct    1140 aaggtaaatt acacaatata tgatggattt aatttaagaa atacaaattt agcagcaaac    1200
tttaatggtc aaaatacaga aattaataat atgaattta ctaaactaaa aaattttact    1260
ggattgtttg aattttatat gttgctatgt gtaagaggga taataacttc taaaactaaa    1320
```

```
tcattagata aaggatacaa taaggcatta aatgatttat gtatcaaagt taataattgg    1380
gacttgtttt ttagtccttc agaagataat tttactaatg atctaaataa aggagaagaa    1440
attacatctg atactaatat agaagcagca gaagaaaata ttagtttaga tttaatacaa    1500
caatattatt taacctttaa ttttgataat gaacctgaaa atatttcaat agaaaatctt    1560
tcaagtgaca ttataggcca attagaactt atgcctaata tagaaagatt tcctaatgga    1620
aaaaagtatg agttagataa atatactatg ttccattatc ttcgtgctca agaatttgaa    1680
catggtaaat ctaggattgc tttaacaaat tctgttaacg aagcattatt aaatcctagt    1740
cgtgtttata cattttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tactttgtca    2040
cttgtatcat atattgcgaa taaggttcta accgttcaaa caatagataa tgctttaagt    2100
aaaagaaatg aaaaatggga tgaggtctat aaatatatag taacaaattg gttagcaaag    2160
gttaatacac agattgatct aataagaaaa aaatgaaag aagctttaga aaatcaagca    2220
gaagcaacaa aggctataat aaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400 atccctatg gtgttaaacg gttagaagat tttgatgcta gtcttaaaga tgcattatta    2460
aagtatatat atgataatag aggaacttta attggtcaag tagatagatt aaaagataaa    2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa aataaatatt    2700
ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa aacaaagagt agttttaaa    3000 tacagtcaaa tgattaatat atcagattat ataaacagat ggattttgt aactatcact    3060 aataatagat taaataactc taaaatttat ataaatggaa gattaataga tcaaaaacca    3120
atttcaaatt taggtaatat tcatgctagt aataatataa tgttaaatt agatggttgt    3180 agagatacac atagatatat ttggataaaa tattttaatc tttttgataa ggaattaaat    3240
gaaaaagaaa tcaaagattt atatgataat caatcaaatt caggtatttt aaaagacttt    3300 tgggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtatagggg acaaaatttt    3480 attataaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
```

-continued

```
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335
```

```
Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
            725                 730                 735

Glu Asn Gln Ala Glu Ala Thr Lys Ala Ile Ile Asn Tyr Gln Tyr Asn
            740                 745                 750
```

```
Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
                850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
                930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155
```

Lys Phe Ile Ile Lys Lys Tyr Ala Ser Gly Asn Lys Asp Asn Ile
1160            1165                1170

Val Arg Asn Asn Asp Arg Val Tyr Ile Asn Val Val Lys Asn
    1175            1180                1185

Lys Glu Tyr Arg Leu Ala Thr Asn Ala Ser Gln Ala Gly Val Glu
    1190            1195                1200

Lys Ile Leu Ser Ala Leu Glu Ile Pro Asp Val Gly Asn Leu Ser
    1205            1210                1215

Gln Val Val Val Met Lys Ser Lys Asn Asp Gln Gly Ile Thr Asn
    1220            1225                1230

Lys Cys Lys Met Asn Leu Gln Asp Asn Asn Gly Asn Asp Ile Gly
    1235            1240                1245

Phe Ile Gly Phe His Gln Phe Asn Asn Ile Ala Lys Leu Val Ala
    1250            1255                1260

Ser Asn Trp Tyr Asn Arg Gln Ile Glu Arg Ser Ser Arg Thr Leu
    1265            1270                1275

Gly Cys Ser Trp Glu Phe Ile Pro Val Asp Asp Gly Trp Gly Glu
    1280            1285                1290

Arg Pro Leu
    1295

<210> SEQ ID NO 3
<211> LENGTH: 3876
<212> TYPE: DNA
<213> ORGANISM: Clostridium botulinum

<400> SEQUENCE: 3
atgccagtta caataaataa ttttaattat aatgatccta ttgataataa taatattatt      60
atgatggagc ctccatttgc gagaggtacg gggagatatt ataaagcttt taaaatcaca     120
gatcgtattt ggataatacc ggaaagatat acttttggat ataaacctga ggattttaat     180
aaaagttccg gtattttaa tagagatgtt tgtgaatatt atgatccaga ttacttaaat      240
actaatgata aaagaatat attttttacaa acaatgatca agttattaa tagaatcaaa     300 tcaaaaccat tgggtgaaaa gttattagag atgattataa atggtatacc ttatcttgga     360
gatagacgtg ttccactcga gagtttaac acaaacattg ctagtgtaac tgttaataaa      420
ttaatcagta atccaggaga agtggagcga aaaaaaggta ttttcgcaaa tttaataata     480
tttggacctg gccagttttt aaatgaaaat gagactatag atataggtat acaaaatcat     540
tttgcatcaa gggaaggctt cggggggtata atgcaaatga agttttgccc agaatatgta     600
agcgtattta taatgttca agaaaacaaa ggcgcaagta tatttaatag acgtggatat      660
ttttcagatc cagccttgat attaatgcat gaacttatac atgttttaca tggattatat     720
ggcattaaag tagatgattt accaattgta ccaaatgaaa aaaaattttt tatgcaatct     780
acagatgcta tacaggcaga agaactatat acatttggag acaagatcc cagcatcata      840 actccttcta cggataaaag tatctatgat aaagttttgc aaaattttag agggatagtt     900
gatagactta acaaggtttt agtttgcata tcagatccta acattaatat taatatatat     960
aaaaataaat ttaagataaa atataaattc gttgaagatt ctgagggaaa atatagtata    1020
gatgtagaaa gttttgataa attatataaa agcttaatgt ttggttttac agaaactaat    1080
atagcagaaa attataaaat aaaaactaga gcttccttatt ttagtgattc cttaccacca    1140
gtaaaaataa aaaattttat tagataatgaa atctatacta tagaggaagg gtttaatata    1200

```
tctgataaag atatggaaaa agaatataga ggtcagaata aagctataaa taaacaagct    1260
tatgaagaaa ttagcaagga gcatttggct gtatataaga tacaaatgtg taaaagtgtt    1320
aaagctccag gaatatgtat tgatgttgat aatgaagatt tgttctttat agctgataaa    1380
aatagttttt cagatgattt atctaaaaac gaaagaatag aatataatac acagagtaat    1440
tatatagaaa atgacttccc tataaatgaa ttaattttag atactgattt aataagtaaa    1500
atagaattac caagtgaaaa tacagaatca cttactgatt ttaatgtaga tgttccagta    1560
tatgaaaaac aacccgctat aaaaaaaatt tttacagatg aaaataccat ctttcaatat    1620
ttatactctc agacatttcc tctagatata agagatataa gtttaacatc ttcatttgat    1680
gatgcattat tattttctaa caaagtttat tcatttttt ctatggatta tattaaaact    1740
gctaataaag tggtagaagc aggattattt gcaggttggg tgaaacagat agtaaatgat    1800
tttgtaatcg aagctaataa aagcaatact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagcctttt attagaatca tatattgaca ataaaaataa aattattaaa    2040
acaatagata atgctttaac taaaagaaat gaaaaatgga gtgatatgta cggattaata    2100
gtagcgcaat ggctctcaac agttaatact caattttata caataaaaga gggaatgtat    2160
aaggctttaa attatcaagc acaagcattg gaagaaataa taaaatacag atataatata    2220
tattctgaaa aagaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaaat gattccatta gctgtagaaa aattactaga ctttgataat    2400
actctcaaaa aaatttgtt aaattatata gatgaaaata aattatattt gattggaagt    2460
gcagaatatg aaaaatcaaa agtaaataaa tacttgaaaa ccattatgcc gtttgatctt    2520
tcaatatata ccaatgatac aatactaata gaaatgttta ataaatataa tagcgaaatt    2580
ttaaataata ttatcttaaa tttaagatat aaggataata atttaataga tttatcagga    2640
tatggggcaa aggtagaggt atatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagcttt tggataagaa tacctaaata taagaatgat    2820
ggtatacaaa attatattca taatgaatat acaataatta attgtatgaa aaataattcg    2880
ggctggaaaa tatctattag gggtaatagg ataaatatgga ctttaattga tataaatgga    2940
aaaaccaaat cggtattttt tgaatataac ataagagaag atatatcaga gtatataaat    3000
agatggtttt ttgtaactat tactaataat ttgaataacg ctaaaattta tattaatggt    3060
aagctagaat caaatacaga tattaaagat ataagagaag ttattgctaa tggtgaaata    3120
atatttaaat tagatggtga tatagataga acacaattta tttggatgaa atatttcagt    3180
atttttaata cggaattaag tcaatcaaat attgaagaaa gatataaaat tcaatcatat    3240
agcgaatatt taaagatttt tggggaaat cctttaatgt acaataaaga atattatatg    3300
tttaatgcgg ggaataaaaa ttcatatatt aaactaaaga aagattcacc tgtaggtgaa    3360 atttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctgat tttttttaatt taaatcaaga gtggagagta    3540
tatacctata aatattttaa gaaagaggaa gaaaaattgt ttttagctcc tataagtgat    3600
```

```
tctgatgagt tttacaatac tatacaaata aagaatatg atgaacagcc aacatatagt      3660
tgtcagttgc ttttaaaaa agatgaagaa agtactgatg ataggatt gattggtatt        3720 catcgtttct acgaatctgg aattgtattt gaagagtata agattattt ttgtataagt      3780 aaatggtact aaaagaggt aaaaaggaaa ccatataatt taaaattggg atgtaattgg      3840
cagtttattc ctaaagatga agggtggact gaataa                               3876
```

<210> SEQ ID NO 4
<211> LENGTH: 1291
<212> TYPE: PRT
<213> ORGANISM: Clostridium botulinum

<400> SEQUENCE: 4

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320
```

```
Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Gly Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735
```

```
Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
        770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu
        1010                1015                1020

Ser Asn Thr Asp Ile Lys Asp Ile Arg Glu Val Ile Ala Asn Gly
        1025                1030                1035

Glu Ile Ile Phe Lys Leu Asp Gly Asp Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Arg Tyr Lys Ile Gln Ser Tyr Ser Glu Tyr
        1070                1075                1080

Leu Lys Asp Phe Trp Gly Asn Pro Leu Met Tyr Asn Lys Glu Tyr
        1085                1090                1095

Tyr Met Phe Asn Ala Gly Asn Lys Asn Ser Tyr Ile Lys Leu Lys
        1100                1105                1110

Lys Asp Ser Pro Val Gly Glu Ile Leu Thr Arg Ser Lys Tyr Asn
        1115                1120                1125

Gln Asn Ser Lys Tyr Ile Asn Tyr Arg Asp Leu Tyr Ile Gly Glu
        1130                1135                1140
```

| | | | | | | | | | | | |
|---|---|---|---|---|---|---|---|---|---|---|---|
|Lys|Phe|Ile|Ile|Arg|Arg|Lys|Ser|Asn|Ser|Gln|Ser|Ile|Asn|Asp|
| |1145| | | |1150| | | |1155| | | | | |

Asp Ile Val Arg Lys Glu Asp Tyr Ile Tyr Leu Asp Phe Phe Asn
    1160            1165            1170

Leu Asn Gln Glu Trp Arg Val Tyr Thr Tyr Lys Tyr Phe Lys Lys
    1175            1180            1185

Glu Glu Glu Lys Leu Phe Leu Ala Pro Ile Ser Asp Ser Asp Glu
    1190            1195            1200

Phe Tyr Asn Thr Ile Gln Ile Lys Glu Tyr Asp Glu Gln Pro Thr
    1205            1210            1215

Tyr Ser Cys Gln Leu Leu Phe Lys Lys Asp Glu Glu Ser Thr Asp
    1220            1225            1230

Glu Ile Gly Leu Ile Gly Ile His Arg Phe Tyr Glu Ser Gly Ile
    1235            1240            1245

Val Phe Glu Glu Tyr Lys Asp Tyr Phe Cys Ile Ser Lys Trp Tyr
    1250            1255            1260

Leu Lys Glu Val Lys Arg Lys Pro Tyr Asn Leu Lys Leu Gly Cys
    1265            1270            1275

Asn Trp Gln Phe Ile Pro Lys Asp Glu Gly Trp Thr Glu
    1280            1285            1290

<210> SEQ ID NO 5
<211> LENGTH: 3843
<212> TYPE: DNA
<213> ORGANISM: Clostridium botulinum

<400> SEQUENCE: 5

```
atgccaataa caattaacaa ctttaattat tcagatcctg ttgataataa aaatattta      60
tatttagata ctcatttaaa tacattagct aatgagcctg aaaaagcctt tcgcattata     120
gggaatatat gggtaatacc cgatagattt tcaagagatt ctaatccaaa tttaaataaa     180
cctcctcgag ttacaagccc taaaagtggt tattatgatc ctaattattt gagtactgat     240
tctgaaaaag atacattttt aaaagaaatt ataaagttat taaaagaat taactctaga     300
gaaataggag aagaattaat atatagactt gcaacagaca tacccttcc tgggaataac      360
aatactccaa ttaatacttt tgattttgat gtagattta acagtgttga tgttaaaact      420
agacaaggta caactgggt taaaactggt agtataaatc ctagtgttat aataactgga      480
cctagagaaa acattataga cccagaaact tctacgttta aattaactaa caatactttt      540
gcggcacaag aaggatttgg tgctttatca ataatttcaa tatcacctag atttatgcta      600
acatatagta atgcaactaa taatgtagga gagggtagat tttctaagtc tgaattttgc      660
atggatccaa tactaatttt aatgcatgaa cttaatcatg caatgcataa tttatatgga      720
atagctatac caaatgatca aagaatttca tctgtaacta gtaatatttt ttattctcaa      780
tataaggtga aattagagta tgcagaaata tatgcatttg gaggtccaac tatagacctt      840
attcctaaaa gtgcaaggaa atattttgag gaaaaaggcat tggattatta tagatccata      900
gctaaaagac ttaatagtat aactactgca atcccttcaa gctttaataa atatatagga     960
gaatataaac agaaactttat tagaaagtat agattcgtag tagaatcttc aggtgaagtt    1020
gcagtagatc gtaataagtt tgctgagtta tataaagaac ttacacaaat atttacagaa    1080
tttaactacg ctaaaatata taatgtacaa aataggaaaa tatatctttc aaatgtatat   1140
actccggta cggcaaatat attagacgat aatgttatg atatacaaaa tggatttaac    1200
atacctaaaa gtaatttaaa tgtactattt atgggtcaaa atttatctcg aaatccagca    1260
```

```
ttaagaaaag tcaatcctga aaatatgctt tatttattta caaaattttg ccataaagca    1320
atagatggta gatcattata taataaaaca ttagattgta gagagctttt agttaaaaat    1380
actgacttac cctttatagg tgatattagt gatatcaaaa ctgatatatt tttaagcaaa    1440
gatattaatg aagaaactga agttatagac tatccggaca atgtttcagt ggatcaagtt    1500
attctcagta agaataccte agaacatgga caactagatt tattataccc tattattgaa    1560
ggtgagagtc aagtattacc gggagagaat caagtctttt atgataatag aactcaaaat    1620
gttgattatt tgaattctta ttattaccta gaatctcaaa aactaagtga taatgttgaa    1680
gattttactt ttacgacatc aattgaggaa gctttggata atagtggaaa agtatatact    1740
tactttccta aactagctga taaagtaaat acgggtgttc aaggtggttt attttttaatg    1800 tgggcaaatg atgtagttga agattttact acaaatattc taagaaaaga tacattagat    1860
aaaatatcag atgtatcagc tattattccc tatataggac ctgcattaaa tataagtaat    1920
tctgtaagaa ggggaaattt tactgaagca tttgcagtta ccggtgtaac tatttttatta    1980 gaagcgtttc aagaatttac aatacctgca cttggtgcat ttgtgattta tagtaaggtt    2040
caagaaagaa acgagattat taaaactata gataattgtt tagaacaaag gattaaaaga    2100
tggaaagatt catatgaatg gatgatagga acgtggttat ccaggattac tactcaattt    2160
aataatataa gttatcaaat gtatgattct ttaaattatc aggcagatgc aatcaaagat    2220
aaaatagatt tagaatataa aaaatactca ggaagtgata agaaaatat aaaaagtcaa    2280 gttgaaaatt taaaaaatag tttagatata aaaatctcgg aagcaatgaa taatataaat    2340
aaatttatac gagaatgttc tgtaacatac ttatttaaaa atatgctccc taagtaatt    2400 gatgaattaa ataagtttga tttaaaaact aaaacagaat taattaatct tatagatagt    2460
cataatatta ttctagttgg tgaagtagat agattaaaag caaaagtaaa tgagagttttt   2520 gaaaatacaa tacccttaa tattttttca tatactaata attctttatt aaaagatata    2580
attaatgaat atttcaatag tattaatgat tcaaaaattt tgagcttaca aaacaaaaaa    2640
aatgctttag tggatacatc aggatataat gcagaagtga ggctagaagg tgatgttcaa    2700
gttaatacga tatatacaaa tgattttaaa ttaagtagtt caggagataa aattatagta    2760
aatttaaata taatatttt atatagcgct atttatgaga actctagtgt tagttttttgg    2820 attaagatat ctaagatt aactaattct cataatgaat atacaataat taatagtata    2880
aaacaaaatt ctgggtggaa attatgtatt aggaatggca atatagaatg gattttacaa    2940
gatattaata gaaagtataa agtttaatt tttgattata gtgaatcatt aagtcataca    3000
ggatatacaa ataaatggtt ttttgttact ataactaata atataatggg gtatatgaaa    3060
ctttatataa atggagaatt aaagcagagt gaaagaattg aagatttaaa tgaggttaag    3120
ttagataaaa ccatagtatt tggaatagat gagaatatag atgagaatca gatgctttgg    3180
attagagatt ttaatattt ttctaaagaa ttaagcaatg aagatattaa tattgtatat    3240
gagggacaaa tattaagaaa tgttattaaa gattattggg gaaatccttt gaagtttgat    3300
acagaatatt atattattaa tgataattat atagataggt atatagcacc taaaagtaat    3360
atacttgtac ttgttcagta tccagataga tctaaattat atactggaaa tcctattact    3420
attaaatcag tatctgataa gaatccttat agtagaattt taaatggaga taatataatg    3480
tttcatatgt tatataatag tgggaaatat atgataataa gagatactga tacaatatat   3540
gcaatagaag gaagagagtg ttcaaaaaat tgtgtatatg cattaaaatt acagagtaat    3600
```

-continued

```
ttaggtaatt atggtatagg tatatttagt ataaaaaata ttgtatctca aaataaatat    3660
tgtagtcaaa ttttctctag ttttatgaaa aatacaatgc ttctagcaga tatatataaa    3720
ccttggagat tttcttttga aaatgcatac acgccagttg cagtaactaa ttatgagaca    3780
aaactattat caacttcatc tttttggaaa tttatttcta gggatccagg atgggtagag    3840
taa                                                                  3843
```

<210> SEQ ID NO 6
<211> LENGTH: 1280
<212> TYPE: PRT
<213> ORGANISM: Clostridium botulinum

<400> SEQUENCE: 6

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Ile Gly Asn Ile Trp Val Ile Pro Asp
            35                  40                  45

Arg Phe Ser Arg Asp Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Leu Ile Tyr Arg Leu Ala Thr
                100                 105                 110

Asp Ile Pro Phe Pro Gly Asn Asn Thr Pro Ile Asn Thr Phe Asp
            115                 120                 125

Phe Asp Val Asp Phe Asn Ser Val Asp Val Lys Thr Arg Gln Gly Asn
        130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320
```

Glu Tyr Lys Gln Lys Leu Ile Arg Lys Tyr Arg Phe Val Val Glu Ser
              325                 330                 335

Ser Gly Glu Val Ala Val Asp Arg Asn Lys Phe Ala Glu Leu Tyr Lys
              340                 345                 350

Glu Leu Thr Gln Ile Phe Thr Glu Phe Asn Tyr Ala Lys Ile Tyr Asn
              355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
              405                 410                 415

Arg Asn Pro Ala Leu Arg Lys Val Asn Pro Glu Asn Met Leu Tyr Leu
              420                 425                 430

Phe Thr Lys Phe Cys His Lys Ala Ile Asp Gly Arg Ser Leu Tyr Asn
              435                 440                 445

Lys Thr Leu Asp Cys Arg Glu Leu Leu Val Lys Asn Thr Asp Leu Pro
450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
              485                 490                 495

Val Asp Gln Val Ile Leu Ser Lys Asn Thr Ser Glu His Gly Gln Leu
              500                 505                 510

Asp Leu Leu Tyr Pro Ile Ile Glu Gly Ser Gln Val Leu Pro Gly
              515                 520                 525

Glu Asn Gln Val Phe Tyr Asp Asn Arg Thr Gln Asn Val Asp Tyr Leu
              530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
              565                 570                 575

Lys Val Tyr Thr Tyr Phe Pro Lys Leu Ala Asp Lys Val Asn Thr Gly
              580                 585                 590

Val Gln Gly Gly Leu Phe Leu Met Trp Ala Asn Asp Val Val Glu Asp
              595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
              645                 650                 655

Thr Ile Leu Leu Glu Ala Phe Gln Glu Phe Thr Ile Pro Ala Leu Gly
              660                 665                 670

Ala Phe Val Ile Tyr Ser Lys Val Gln Glu Arg Asn Glu Ile Ile Lys
              675                 680                 685

Thr Ile Asp Asn Cys Leu Glu Gln Arg Ile Lys Arg Trp Lys Asp Ser
              690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
              725                 730                 735

-continued

Ala Ile Lys Asp Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Ile Lys Ile Ser Glu Ala Met Asn Asn Ile Asn Lys Phe Ile Arg
                770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
                820                 825                 830

Lys Ala Lys Val Asn Glu Ser Phe Glu Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
                900                 905                 910

Ser Ser Gly Asp Lys Ile Ile Val Asn Leu Asn Asn Asn Ile Leu Tyr
                915                 920                 925

Ser Ala Ile Tyr Glu Asn Ser Ser Val Ser Phe Trp Ile Lys Ile Ser
                930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
                980                 985                 990

Tyr Ser Glu Ser Leu Ser His Thr Gly Tyr Thr Asn Lys Trp Phe Phe
                995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
    1130                1135                1140

| | | | | | | | | | | |
|---|---|---|---|---|---|---|---|---|---|---|
| Val | Ser | Asp | Lys | Asn | Pro | Tyr | Ser | Arg | Ile | Leu | Asn | Gly | Asp | Asn |
| | 1145 | | | | 1150 | | | | | 1155 | | | | |

Val Ser Asp Lys Asn Pro Tyr Ser Arg Ile Leu Asn Gly Asp Asn
    1145                      1150                      1155

Ile Met Phe His Met Leu Tyr Asn Ser Gly Lys Tyr Met Ile Ile
    1160                      1165                      1170

Arg Asp Thr Asp Thr Ile Tyr Ala Ile Glu Gly Arg Glu Cys Ser
    1175                      1180                      1185

Lys Asn Cys Val Tyr Ala Leu Lys Leu Gln Ser Asn Leu Gly Asn
    1190                      1195                      1200

Tyr Gly Ile Gly Ile Phe Ser Ile Lys Asn Ile Val Ser Gln Asn
    1205                      1210                      1215

Lys Tyr Cys Ser Gln Ile Phe Ser Ser Phe Met Lys Asn Thr Met
    1220                      1225                      1230

Leu Leu Ala Asp Ile Tyr Lys Pro Trp Arg Phe Ser Phe Glu Asn
    1235                      1240                      1245

Ala Tyr Thr Pro Val Ala Val Thr Asn Tyr Glu Thr Lys Leu Leu
    1250                      1255                      1260

Ser Thr Ser Ser Phe Trp Lys Phe Ile Ser Arg Asp Pro Gly Trp
    1265                      1270                      1275

Val Glu
    1280

<210> SEQ ID NO 7
<211> LENGTH: 3858
<212> TYPE: DNA
<213> ORGANISM: Clostridium botulinum

<400> SEQUENCE: 7

```
atgacatggc cagtaaaaga ttttaattat agtgatcctg ttaatgacaa tgatatatta      60
tatttaagaa taccacaaaa taagttaatt actacacctg taaaagcttt tatgattact     120
caaaatattt gggtaatacc agaaagattt catcagata ctaatccaag tttaagtaaa     180
ccgcctagac tacttcaaa gtatcaaagt tattatgatc ctagttattt atctactgat     240
gagcaaaaag atacattttt aaagggatt ataaaattat ttaaaagaat taatgaaaga     300
gatataggaa aaaattaat aaattattta gtagttggtt cacctttat gggagattca     360
agtacgcctg aagatacatt tgattttaca cgtcatacta ctaatattgc agttgaaaag     420
tttgaaaatg gtagttggaa agtaacaaat attataacac aagtgtatt gatatttgga     480
ccacttccta atatattaga ctatacagca tcccttacat tgcaaggaca acaatcaaat     540
ccatcatttg aagggtttgg aacattatct atactaaaag tagcacctga atttttgtta     600
acatttagtg atgtaacatc taatcaaagt tcagctgtat taggcaaatc tatattttgt     660
atggatccag taatagcttt aatgcatgag ttaacacatt ctttgcatca attgtatgga     720
ataaatatac catctgataa aaggattcgt ccacaagtta gcgagggatt ttttctcaa     780
gatggaccca acgtacaatt tgaggaatta tacacatttg gaggatcaga tgttgaaata     840
atacctcaaa ttgaaagatt acaattaaga gaaaaagcat taggtcacta taagatata     900
gcgaaaagac ttaataatat taataaaact attccttcta gttggagtag taatatagat     960
aaatataaaa aaatatttc tgaaaagtat aattttgata agataatac aggaaatttt    1020
gttgtaaata ttgataaatt caatagctta tattcagact tgactaatgt tatgtcagaa    1080
gttgtttatt cttcgcaata taatgttaaa acaggactc attatttttc aaagcattat    1140
ctacctgtat ttgcaaatat attagatgat aatatttata ctataatcaa cggttttaat    1200
```

```
ttaacaacta aaggttttaa tatagaaaat tcgggtcaga atatagaaag gaatcctgca      1260
ctacaaaaac ttagttcaga aagtgtagta gatttgttta caaaagtatg tttaagatta      1320
acaagaaata gtagagatga ttcaacatgt attcaagtta aaaataatac attaccttat      1380
gtagctgata aagatagcat ttcacaagaa atatttgaaa gtcaaattat tacagatgag      1440
actaatgtag aaaattattc agataatttt tcattagatg aatctatttt agatgcaaaa      1500
gtccctacta atcctgaagc agtagatcca ctgttaccca atgttaatat ggaaccttta      1560
aatgttccag gtgaagaaga agtattttat gatgatatta ctaaagatgt tgattattta      1620
aactcttatt attatttgga agcccaaaaa ttaagtaata atgttgaaaa tattactctt      1680
acaacttcag ttgaagaagc attaggttat agcaataaga tatacacatt tttacctagc      1740
ttagctgaaa aagtgaataa aggtgttcaa gcaggtttat tcttaaattg ggcgaatgaa      1800
gtagttgagg attttactac aaatattatg aaaaaagata cattggataa aatatcagat      1860
gtatcagcca taattccata tataggacct gccttaaata taggaaattc agcattaagg      1920
ggaaacttta agcaagcatt tgcaacagct ggtgtagctt ttttgttaga aggatttcca      1980
gagtttacaa tacctgcact cggtgtattt accttttata gttctattca agaaagagag      2040
aaaattatta aaactataga aaattgttta gaacaaagag ttaagagatg gaaagattca      2100
tatcaatgga tggtatcaaa ttggttgtca agaattacta ctcgatttaa tcatataagt      2160
tatcaaatgt atgattcttt gagttatcag gcagatgcaa tcaaagctaa aatagattta      2220
gaatataaaa aatactcagg aagtgataaa gaaaatataa aaagtcaagt tgaaaattta      2280
aaaaatagtt tagatgtaaa aatctcggaa gcaatgaata atataaataa atttatacga      2340
gaatgttctg taacatactt atttaaaaat atgctcccta aagtaattga tgaattaaat      2400
aagtttgatt taaaaactaa aacagaatta attaatctta tagatagtca taatattatt      2460
ctagttggtg aagtagatag attaaaagca aagtaaatg agagttttga aaatacaata      2520
ccctttaata ttttttcata tactaataat tctttattaa aagatatgat taatgaatat      2580
ttcaatagta ttaatgattc aaaaattttg agcttacaaa ataaaaaaaa tactttgatg      2640
gatacatcag gatataacgc agaagtgaga gtagaaggca atgttcagct taatccaata      2700
tttccatttg actttaaatt aggtagttca ggggatgata gaggtaaagt tatagtaacc      2760
cagaatgaaa atattgtata taatgctatg tatgaaagtt ttagtattag tttttggatt      2820
aggataaata aatgggtaag taatttacct ggatatacta taattgatag tgttaaaaat      2880
aactcaggtt ggagtatagg tattattagt aattttttag tgtttacttt aaaacaaaat      2940
gaaaatagtg aacaagatat aaactttagt tatgatatat caaagaatgc tgcgggatat      3000
aataaatggt tttttgtaac tattactacc aatatgatgg gaaatatgat gatttatata      3060
aatggaaaat taatagatac tataaaagtt aaagagttaa ctggaattaa ttтттagcaaa      3120 actataacat ttcaaatgaa taaaattcca aatactggct taattacctc agattctgat      3180
aacatcaata tgtggataag ggattttta atctttgcta agaattaga tgataaagat      3240 attaatatat tatttaatag cttgcaatat actaatgttg taaaagatta ttggggaaat      3300
gatttaagat atgataaaga atattacatg attaacgtaa attatatgaa tagatatatg      3360
tctaaaaaag gcaatggaat tgtttttaat acacgtaaaa ataataatga cttcaatgaa      3420
ggatataaaa ttataataaa aagaattaga ggaaatacaa atgatactag agtcgcgagga      3480 gaaaatgtat tatattttaa tactacaatt gataacaaac aatatagttt aggtatgtat      3540
aaaccttcta gaaatctagg gactgattta gttccactag gtgcattgga tcaaccaatg      3600
```

-continued

```
gatgagatac gtaaatatgg ttcgtttata atacaaccat gcaatacttt tgattactat    3660
gcatcacaat tatttttgtc aagtaatgca acaacaaata ggcttggaat actatcaatt    3720
ggtagttata gtttcaaact tggagatgac tattggttta atcacgaata tttaattcct    3780
gttataaaaa tagagcatta tgcttcatta ttagaatcaa catcaactca ttgggttttt    3840
gtacctgcaa gtgaataa                                                   3858
```

<210> SEQ ID NO 8
<211> LENGTH: 1285
<212> TYPE: PRT
<213> ORGANISM: Clostridium botulinum

<400> SEQUENCE: 8

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ser Asn Ile Asp
305                 310                 315                 320
```

-continued

Lys Tyr Lys Lys Ile Phe Ser Glu Lys Tyr Asn Phe Asp Lys Asp Asn
                    325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
                355                 360                 365

Val Lys Asn Arg Thr His Tyr Phe Ser Lys His Tyr Leu Pro Val Phe
370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Arg Asn Ser Arg Asp Asp Ser
                435                 440                 445

Thr Cys Ile Gln Val Lys Asn Asn Thr Leu Pro Tyr Val Ala Asp Lys
        450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
                500                 505                 510

Pro Asn Val Asn Met Glu Pro Leu Asn Val Pro Gly Glu Glu Glu Val
                515                 520                 525

Phe Tyr Asp Asp Ile Thr Lys Asp Val Asp Tyr Leu Asn Ser Tyr Tyr
                530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
                595                 600                 605

Ile Met Lys Lys Asp Thr Leu Asp Lys Ile Ser Asp Val Ser Ala Ile
                610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
                675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

```
Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
            770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
            835                 840                 845

Asn Asn Ser Leu Leu Lys Asp Met Ile Asn Glu Tyr Phe Asn Ser Ile
            850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
            915                 920                 925

Ala Met Tyr Glu Ser Phe Ser Ile Ser Phe Trp Ile Arg Ile Asn Lys
            930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
            995                1000                1005

Thr Thr Asn Met Met Gly Asn Met Met Ile Tyr Ile Asn Gly Lys
            1010                1015                1020

Leu Ile Asp Thr Ile Lys Val Lys Glu Leu Thr Gly Ile Asn Phe
            1025                1030                1035

Ser Lys Thr Ile Thr Phe Gln Met Asn Lys Ile Pro Asn Thr Gly
            1040                1045                1050

Leu Ile Thr Ser Asp Ser Asp Asn Ile Asn Met Trp Ile Arg Asp
            1055                1060                1065

Phe Tyr Ile Phe Ala Lys Glu Leu Asp Asp Lys Asp Ile Asn Ile
            1070                1075                1080

Leu Phe Asn Ser Leu Gln Tyr Thr Asn Val Val Lys Asp Tyr Trp
            1085                1090                1095

Gly Asn Asp Leu Arg Tyr Asp Lys Glu Tyr Tyr Met Ile Asn Val
            1100                1105                1110

Asn Tyr Met Asn Arg Tyr Met Ser Lys Lys Gly Asn Gly Ile Val
            1115                1120                1125

Phe Asn Thr Arg Lys Asn Asn Asn Asp Phe Asn Glu Gly Tyr Lys
            1130                1135                1140
```

```
Ile Ile Ile Lys Arg Ile Arg Gly Asn Thr Asn Asp Thr Arg Val
    1145                1150                1155

Arg Gly Glu Asn Val Leu Tyr Phe Asn Thr Thr Ile Asp Asn Lys
    1160                1165                1170

Gln Tyr Ser Leu Gly Met Tyr Lys Pro Ser Arg Asn Leu Gly Thr
    1175                1180                1185

Asp Leu Val Pro Leu Gly Ala Leu Asp Gln Pro Met Asp Glu Ile
    1190                1195                1200

Arg Lys Tyr Gly Ser Phe Ile Ile Gln Pro Cys Asn Thr Phe Asp
    1205                1210                1215

Tyr Tyr Ala Ser Gln Leu Phe Leu Ser Ser Asn Ala Thr Thr Asn
    1220                1225                1230

Arg Leu Gly Ile Leu Ser Ile Gly Ser Tyr Ser Phe Lys Leu Gly
    1235                1240                1245

Asp Asp Tyr Trp Phe Asn His Glu Tyr Leu Ile Pro Val Ile Lys
    1250                1255                1260

Ile Glu His Tyr Ala Ser Leu Leu Glu Ser Thr Ser Thr His Trp
    1265                1270                1275

Val Phe Val Pro Ala Ser Glu
    1280                1285

<210> SEQ ID NO 9
<211> LENGTH: 3756
<212> TYPE: DNA
<213> ORGANISM: Clostridium botulinum

<400> SEQUENCE: 9
atgccaaaaa ttaatagttt taattataat gatcctgtta atgatagaac aattttatat      60
attaaaccag gcggttgtca agaattttat aaatcattta atattatgaa aaatatttgg     120
ataattccag agagaaatgt aattggtaca accccccaag attttcatcc gcctacttca     180
ttaaaaaatg gagatagtag ttattatgac cctaattatt tacaaagtga tgaagaaaag     240
gatagatttt taaaaatagt cacaaaaata tttaatagaa taataataa tctttcagga     300 gggattttat tagaagaact gtcaaaagct aatccatatt tagggaatga taatactcca     360
gataatcaat tccatattgg tgatgcatca gcagttgaga ttaaattctc aaatggtagc     420
caagacatac tattacctaa tgttattata atgggagcag agcctgattt atttgaaact     480
aacagttcca atatttctct aagaaataat tatatgccaa gcaatcaccg ttttggatca     540
atagctatag taacattctc acctgaatat tcttttagat ttaatgataa ttgtatgaat     600
gaatttattc aagatcctgc tcttacatta atgcatgaat aatacattc attacatgga     660 ctatatgggg ctaaagggat tactacaaag tatactataa cacaaaaaca aaatccccta     720
ataacaaata taagaggtac aaatattgaa gaattcttaa cttttggagg tactgattta     780
aacattatta ctagtgctca gtccaatgat atctatacta atcttctagc tgattataaa     840
aaaatagcgt ctaaacttag caaagtacaa gtatctaatc cactacttaa tcctataaaa     900
gatgtttttg aagcaaagta tggattagat aaagatgcta gcggaattta ttcggtaaat     960
ataaacaaat ttaatgatat ttttaaaaaa ttatacagct ttacggaatt tgatttacga    1020
actaaatttc aagttaaatg taggcaaact tatattggac agtataaata cttcaaactt    1080
tcaaacttgt taaatgattc tatttataat atatcagaag ctataatat aaataattta    1140 aaggtaaatt ttagaggaca gaatgcaaat ttaaatccta gaattattac accaattaca    1200
ggtagaggac tagtaaaaaa aatcattaga ttttgtaaaa atattgtttc tgtaaaaggc    1260
```

```
ataaggaaat caatatgtat cgaaataaat aatggtgagt tattttttgt ggcttccgag    1320
aatagttata atgatgataa tataaatact cctaaagaaa ttgacgatac agtaacttca    1380
aataataatt atgaaaatga tttagatcag gttattttaa attttaatag tgaatcagca    1440
cctggacttt cagatgaaaa attaaattta actatccaaa atgatgctta tataccaaaa    1500
tatgattcta atggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat ttttttcatc agaatttatt    1680
aataatgtca ataaacctgt gcaagcagca ttatttgtaa gctggataca acaagtgtta    1740 gtagattta ctactgaagc taaccaaaaa agtactgttg ataaaattgc agatatttct    1800
atagttgttc catatatagg tcttgcttta aatataggaa atgaagcaca aaaggaaat    1860 tttaaagatg cacttgaatt attaggagca ggtatttat tagaatttga acccgagctt    1920
ttaattccta caattttagt attcacgata aaatctttt taggttcatc tgataataaa    1980
aataaagtta ttaaagcaat aaataatgca ttgaaagaaa gagatgaaaa atggaaagaa    2040
gtatatagtt ttatagtatc gaattggatg actaaaatta atacacaatt taataaaaga    2100
aaagaacaaa tgtatcaagc tttacaaaat caagtaaatg caattaaaac aataatagaa    2160
tctaagtata atagttatac tttagaggaa aaaaatgagc ttacaaataa atatgatatt    2220
aagcaaatag aaaatgaact taatcaaaag gtttctatag caatgaataa tatagacagg    2280
ttcttaactg aaagttctat atcctattta atgaaaataa taaatgaagt aaaaattaat    2340
aaattaagag aatatgatga gaatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaattttaat ttcatatttt    2520
aataaattct ttaagagaat taaaagtagt tcagttttaa atatgagata taaaaatgat    2580
aaatacgtag atacttcagg atatgattca aatataaata ttaatggaga tgtatataaa    2640
tatccaacta ataaaaatca atttggaata tataatgata aacttagtga agttaatata    2700
tctcaaaatg attacattat atatgataat aaatataaaa attttagtat tagttttggg    2760
gtaagaattc ctaactatga taataagata gtaaatgtta ataatgaata cactataata    2820
aattgtatga gagataataa ttcaggatgg aaagtatctc ttaatcataa tgaaataatt    2880
tggacattcg aagataatcg aggaattaat caaaaattag catttaacta tggtaacgca    2940 aatggtatt ctgattatat aaataagtgg attttttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatattttt gataaagaat tagatgaaac agaaattcaa    3180
actttatata gcaatgaacc taatacaaat attttgaagg attttggggg aaattatttg    3240
ctttatgaca aagaatacta tttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttattt    3480
ccattatatg ctgatacagc taccacaaat aaagagaaaa caataaaaat atcatcatct    3540
ggcaatagat ttaatcaagt agtagttatg aattcagtag gaaattgtac aatgaatttt    3600
```

```
aaaaataata atggaaataa tattgggttg ttaggtttca aggcagatac tgtcgttgct    3660
agtacttggt attatacaca tatgagagat catacaaaca gcaatggatg tttttggaac    3720
tttatttctg aagaacatgg atggcaagaa aaataa                              3756
```

<210> SEQ ID NO 10
<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350
```

```
Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
        450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
                660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
        690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
                740                 745                 750

Ile Ala Met Asn Asn Ile Asp Arg Phe Leu Thr Glu Ser Ser Ile Ser
            755                 760                 765
```

-continued

```
Tyr Leu Met Lys Ile Ile Asn Glu Val Lys Ile Asn Lys Leu Arg Glu
    770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                    805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
        835                 840                 845
Ser Ser Ser Val Leu Asn Met Arg Tyr Lys Asn Asp Lys Tyr Val Asp
850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                    885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
        915                 920                 925
Lys Ile Val Asn Val Asn Asn Glu Tyr Thr Ile Ile Asn Cys Met Arg
930                 935                 940
Asp Asn Asn Ser Gly Trp Lys Val Ser Leu Asn His Asn Glu Ile Ile
945                 950                 955                 960
Trp Thr Phe Glu Asp Asn Arg Gly Ile Asn Gln Lys Leu Ala Phe Asn
                    965                 970                 975
Tyr Gly Asn Ala Asn Gly Ile Ser Asp Tyr Ile Asn Lys Trp Ile Phe
                980                 985                 990
Val Thr Ile Thr Asn Asp Arg Leu  Gly Asp Ser Lys Leu  Tyr Ile Asn
        995                 1000                1005
Gly Asn  Leu Ile Asp Gln Lys  Ser Ile Leu Asn Leu  Gly Asn Ile
    1010                1015                1020
His Val  Ser Asp Asn Ile Leu  Phe Lys Ile Val Asn  Cys Ser Tyr
    1025                1030                1035
Thr Arg  Tyr Ile Gly Ile Arg  Tyr Phe Asn Ile Phe  Asp Lys Glu
    1040                1045                1050
Leu Asp  Glu Thr Glu Ile Gln  Thr Leu Tyr Ser Asn  Glu Pro Asn
    1055                1060                1065
Thr Asn  Ile Leu Lys Asp Phe  Trp Gly Asn Tyr Leu  Leu Tyr Asp
    1070                1075                1080
Lys Glu  Tyr Tyr Leu Leu Asn  Val Leu Lys Pro Asn  Asn Phe Ile
    1085                1090                1095
Asp Arg  Arg Lys Asp Ser Thr  Leu Ser Ile Asn Asn  Ile Arg Ser
    1100                1105                1110
Thr Ile  Leu Leu Ala Asn Arg  Leu Tyr Ser Gly Ile  Lys Val Lys
    1115                1120                1125
Ile Gln  Arg Val Asn Asn Ser  Ser Thr Asn Asp Asn  Leu Val Arg
    1130                1135                1140
Lys Asn  Asp Gln Val Tyr Ile  Asn Phe Val Ala Ser  Lys Thr His
    1145                1150                1155
Leu Phe  Pro Leu Tyr Ala Asp  Thr Ala Thr Thr Asn  Lys Glu Lys
    1160                1165                1170
```

```
Thr Ile Lys Ile Ser Ser Gly Asn Arg Phe Asn Gln Val Val
    1175            1180                1185

Val Met Asn Ser Val Gly Asn Cys Thr Met Asn Phe Lys Asn Asn
    1190            1195                1200

Asn Gly Asn Asn Ile Gly Leu Leu Gly Phe Lys Ala Asp Thr Val
    1205            1210                1215

Val Ala Ser Thr Trp Tyr Tyr Thr His Met Arg Asp His Thr Asn
    1220            1225                1230

Ser Asn Gly Cys Phe Trp Asn Phe Ile Ser Glu Glu His Gly Trp
    1235            1240                1245

Gln Glu Lys
    1250

<210> SEQ ID NO 11
<211> LENGTH: 3843
<212> TYPE: DNA
<213> ORGANISM: Clostridium botulinum

<400> SEQUENCE: 11
```

| | | | | | |
|---|---|---|---|---|---|
| atgccagttg | taataaatag | ttttaattat | aatgaccctg | ttaatgatga | gacaattta | 60 |
| tacatgcaga | aaccatatga | agaaagaagt | agaaaatatt | ataaagcttt | tgagattatg | 120 |
| cctaatgttt | ggataatgcc | tgagagagat | acaataggaa | ctaagcctga | tgagtttcag | 180 |
| gtgccggatt | cattaaagaa | cggaagtagt | gcttattatg | atcctaatta | tttaaccact | 240 |
| gatgctgaaa | aagatagata | tttaaaaaca | atgataaaat | tatttaatag | aattaatagt | 300 |
| aatcctacag | ggaaagtttt | gttagaagaa | gtatcaaatg | ctagaccata | tttaggagat | 360 |
| gatgacacgc | taattaatga | attccttcca | gttaatgtaa | ctacaagtgt | taatataaaa | 420 |
| ttttcaactg | atgttgaaag | tcaataata | tcgaatcttc | ttgtattggg | agcaggacct | 480 |
| gatatattta | agcttactg | tacccccctt | gtaaggttta | ataagtcaga | taaattaatt | 540 |
| gaaccaagta | atcatggttt | tggatcaatt | aatatcttga | cattttcacc | tgagtatgaa | 600 |
| catatttta | atgatattag | tggagggaat | cataatagta | cagaatcatt | tattgcagat | 660 |
| cctgcaattt | cactagctca | tgaattgata | catgcactac | atggattata | cggggctaag | 720 |
| gcagttactc | ataaagagtc | tctagtagca | gagcgaggac | ctcttatgat | agccgaaaag | 780 |
| cccataaggc | tagaagaatt | tttaactttt | ggaggtgagg | atttaaatat | cattcctagt | 840 |
| gctatgaagg | aaaaaatata | taacgatctt | ttagctaact | atgaaaaaat | agctactaga | 900 |
| cttagagaag | ttaatacggc | tcctcctgga | tatgatatta | tgaatataa | agattattt | 960 |
| caatggaagt | atggactaga | tagaaatgca | gatggaagtt | atactgtgaa | tagaaataaa | 1020 |
| tttaatgaaa | tttataaaa | attatatagc | tttacagaga | ttgacttagc | aaataaattt | 1080 |
| aaagtaaaat | gtagaaatac | ttattttatt | aaatatggat | ttgtaaaagt | tccaaatttg | 1140 |
| ttagatgatg | atatttatac | tgtatcagag | gggtttaata | taggtaattt | agcagtaaac | 1200 |
| aatcgcggac | aaaatataaa | tttaaatcct | aaaattattg | attccattcc | agataaaggt | 1260 |
| ttagtggaaa | agattattaa | atttgtaag | agcattattc | ctagaaaagg | tacgaagcag | 1320 |
| tcaccgtcac | tatgcattag | agtaaataat | agggagttat | tttttgtagc | ttcagaaagt | 1380 |
| agctataatg | aaagtgatat | taatacacct | aaagaattg | acgatacaac | aaatctaaat | 1440 |
| aataattata | gaaataattt | agtgaagtt | attttagatt | ataatagtga | gacaatacct | 1500 |
| caaatatcaa | atcgaacatt | aaatacactt | gtacaagaca | atagttatgt | gccaagatat | 1560 |

```
gattctaatg gaacaagtga aatagaggaa tatgatgttg ttgactttaa tgtatttttc    1620
tatttacatg cacaaaaagt accagaaggt gaaaccaata taagtttaac ttcttcaatt    1680
gatacagcat tattagaaga atccaaagta tatacatttt tttcttcaga gtttatcgat    1740
actatcaata aacctgtaaa tgcagcacta tttatagatt ggataagcaa agtaataaga    1800
gattttacca ctgaagctac acaaaaaagt actgttgata agattgcaga catatcttta    1860
attgtaccct atgtaggtct tgctttgaat atagttattg aggcagaaaa aggaaatttt    1920
gaggaggcat ttgaattatt aggagcgggt attttattag aatttgtgcc agagcttaca    1980
attcctgtaa ttttagtgtt tacgataaaa tcctatatag attcatatga gaataaaaat    2040
aaagcaatta aagcaataaa taattcatta atcgaaagag aagcaaagtg gaaagaaata    2100
tatagttgga tagtatcaaa ttggcttact agaattaata cgcaatttaa taaaagaaaa    2160
gagcaaatgt atcaggcttt acaaaatcaa gtagatgcaa taaaaacagc aatagaatat    2220
aaatataata attatacttc agatgagaaa aatagacttg aatctaaata taatatcaat    2280
aatatagaag aagaattgaa taaaaaagtt tctttagcaa tgaaaaatat agaaagattt    2340
atgacagaaa gttctatatc ttatttaatg aaattaataa atgaagccga agttggtaaa    2400
ttaaaagaat atgataaaca tgttaagagc gatttattag actatattct ctaccataaa    2460
ttaatcttag gagagcagac aaaggaatta attgatttgg tgactagtac tttgaatagt    2520
agtattccat ttgaactttc ttcatatact aatgataaaa ttctaattat atattttaat    2580
agattatata aaaaaattaa agatagttct attttagata tgcgatatga aaataataaa    2640
tttatagata tctctggata tggttcaaat ataagcatta atggaaacgt atatatttat    2700
tcaacaaata gaaatcaatt tggaatatat agtggtaggc ttagtgaagt taatatagct    2760
caaaataatg atattatata caatagtaga tatcaaaatt ttagtattag tttctgggta    2820
accattccta aacactacag acctatgaat cgtaatcggg aatacactat aataaattgt    2880
atggggaata taattcgggg atggaaaata tcacttagaa ctattagaga ttgtgaaata    2940
atttggactt tacaagatac ttccggaaat aaggaaaaat taatttttag gtatgaagaa    3000
cttgctagta tatctgatta tataaataaa tggattttg taactattac taataataga    3060
ttaggcaatt ctagaattta catcaatgga aatttaatag ttgaaaaatc aatttcgaat    3120
ttaggtgata ttcatgttag tgataatata ttatttaaaa ttgttggttg tgatgatgaa    3180
acgtatgttg gtataagata ttttaaagtt tttaatacgg aattagataa aacagaaatt    3240
gagactttat atagtaatga gccagatcca agtatcttaa aagactattg gggaaattat    3300
ttgctatata ataaaaaata ttatttattc aatttactaa gaaaagataa gtatattact    3360
cggaattcag gcattttaaa tattaatcaa caaagaggtg ttactggagg catatctgtt    3420
tttttgaact ataaattata tgaaggagta gaagttatta taagaaaaaa tgctcctata    3480
gatatatcta atacagataa ttttgttaga aaaaacgatc tagcatacat taatgtagta    3540
gatcatggtg tagaatatcg gttatatgct gatatatcaa ttacaaaatc agagaaaata    3600
ataaaattaa taagaacatc taatccaaac gatagcttag gtcaaattat agttatggat    3660
tcaataggaa ataattgcac aatgaatttt caaaacaatg atgggagcaa tataggatta    3720
ctaggttttc attcagatga tttggttgct agtagttggt attataacca tatacgaaga    3780
aacactagca gtaatggatg ctttttggagt tttatttcta aagagcatgg ttggaaagaa    3840
taa                                                                 3843
```

<210> SEQ ID NO 12
<211> LENGTH: 1280
<212> TYPE: PRT
<213> ORGANISM: Clostridium botulinum

<400> SEQUENCE: 12

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Thr Leu Ile Asn Glu Phe
        115                 120                 125

Leu Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asn Leu Leu Asp Asp Asp
    370                 375                 380

-continued

```
Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
            405                 410                 415

Pro Asp Lys Gly Leu Val Glu Lys Ile Ile Lys Phe Cys Lys Ser Ile
        420                 425                 430

Ile Pro Arg Lys Gly Thr Lys Gln Ser Pro Ser Leu Cys Ile Arg Val
    435                 440                 445

Asn Asn Arg Glu Leu Phe Phe Val Ala Ser Glu Ser Tyr Asn Glu
450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
        500                 505                 510

Asp Asn Ser Tyr Val Pro Arg Tyr Asp Ser Asn Gly Thr Ser Glu Ile
    515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
            565                 570                 575

Glu Phe Ile Asp Thr Ile Asn Lys Pro Val Asn Ala Ala Leu Phe Ile
        580                 585                 590

Asp Trp Ile Ser Lys Val Ile Arg Asp Phe Thr Thr Glu Ala Thr Gln
    595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
            645                 650                 655

Pro Glu Leu Thr Ile Pro Val Ile Leu Val Phe Thr Ile Lys Ser Tyr
        660                 665                 670

Ile Asp Ser Tyr Glu Asn Lys Asn Lys Ala Ile Lys Ala Ile Asn Asn
    675                 680                 685

Ser Leu Ile Glu Arg Glu Ala Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Ala Ile Glu Tyr Lys Tyr Asn Asn Tyr Thr Ser Asp Glu Lys Asn Arg
        740                 745                 750

Leu Glu Ser Lys Tyr Asn Ile Asn Asn Ile Glu Glu Leu Asn Lys
    755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800
```

```
Leu Lys Glu Tyr Asp Lys His Val Lys Ser Asp Leu Asp Tyr Ile
            805                 810                 815
Leu Tyr His Lys Leu Ile Leu Gly Glu Gln Thr Lys Glu Leu Ile Asp
            820                 825                 830
Leu Val Thr Ser Thr Leu Asn Ser Ser Ile Pro Phe Glu Leu Ser Ser
            835                 840                 845
Tyr Thr Asn Asp Lys Ile Leu Ile Ile Tyr Phe Asn Arg Leu Tyr Lys
            850                 855                 860
Lys Ile Lys Asp Ser Ser Ile Leu Asp Met Arg Tyr Glu Asn Asn Lys
865                 870                 875                 880
Phe Ile Asp Ile Ser Gly Tyr Gly Ser Asn Ile Ser Ile Asn Gly Asn
            885                 890                 895
Val Tyr Ile Tyr Ser Thr Asn Arg Asn Gln Phe Gly Ile Tyr Ser Gly
            900                 905                 910
Arg Leu Ser Glu Val Asn Ile Ala Gln Asn Asn Asp Ile Ile Tyr Asn
            915                 920                 925
Ser Arg Tyr Gln Asn Phe Ser Ile Ser Phe Trp Val Thr Ile Pro Lys
            930                 935                 940
His Tyr Arg Pro Met Asn Arg Asn Arg Glu Tyr Thr Ile Ile Asn Cys
945                 950                 955                 960
Met Gly Asn Asn Asn Ser Gly Trp Lys Ile Ser Leu Arg Thr Ile Arg
            965                 970                 975
Asp Cys Glu Ile Ile Trp Thr Leu Gln Asp Thr Ser Gly Asn Lys Glu
            980                 985                 990
Lys Leu Ile Phe Arg Tyr Glu Glu Leu Ala Ser Ile Ser Asp Tyr Ile
            995                 1000                1005
Asn Lys Trp Ile Phe Val Thr Ile Thr Asn Asn Arg Leu Gly Asn
            1010                1015                1020
Ser Arg Ile Tyr Ile Asn Gly Asn Leu Ile Val Glu Lys Ser Ile
            1025                1030                1035
Ser Asn Leu Gly Asp Ile His Val Ser Asp Asn Ile Leu Phe Lys
            1040                1045                1050
Ile Val Gly Cys Asp Asp Glu Thr Tyr Val Gly Ile Arg Tyr Phe
            1055                1060                1065
Lys Val Phe Asn Thr Glu Leu Asp Lys Thr Glu Ile Glu Thr Leu
            1070                1075                1080
Tyr Ser Asn Glu Pro Asp Pro Ser Ile Leu Lys Asp Tyr Trp Gly
            1085                1090                1095
Asn Tyr Leu Leu Tyr Asn Lys Lys Tyr Tyr Leu Phe Asn Leu Leu
            1100                1105                1110
Arg Lys Asp Lys Tyr Ile Thr Arg Asn Ser Gly Ile Leu Asn Ile
            1115                1120                1125
Asn Gln Gln Arg Gly Val Thr Gly Gly Ile Ser Val Phe Leu Asn
            1130                1135                1140
Tyr Lys Leu Tyr Glu Gly Val Glu Val Ile Ile Arg Lys Asn Ala
            1145                1150                1155
Pro Ile Asp Ile Ser Asn Thr Asp Asn Phe Val Arg Lys Asn Asp
            1160                1165                1170
Leu Ala Tyr Ile Asn Val Val Asp His Gly Val Glu Tyr Arg Leu
            1175                1180                1185
Tyr Ala Asp Ile Ser Ile Thr Lys Ser Glu Lys Ile Ile Lys Leu
            1190                1195                1200
```

```
Ile Arg Thr Ser Asn Pro Asn Asp Ser Leu Gly Gln Ile Ile Val
1205                 1210                1215

Met Asp Ser Ile Gly Asn Asn Cys Thr Met Asn Phe Gln Asn Asn
1220                 1225                1230

Asp Gly Ser Asn Ile Gly Leu Leu Gly Phe His Ser Asp Asp Leu
1235                 1240                1245

Val Ala Ser Ser Trp Tyr Tyr Asn His Ile Arg Arg Asn Thr Ser
1250                 1255                1260

Ser Asn Gly Cys Phe Trp Ser Phe Ile Ser Lys Glu His Gly Trp
1265                 1270                1275

Lys Glu
1280

<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13
atgccagtta atataaaaan ctttaattat aatgaccta ttaataatga tgacattatt      60
atgatggaac cattcaatga cccagggcca ggaacatatt ataaagcttt taggattata     120
gatcgtattt ggatagtacc agaaaggttt acttatggat ttcaacctga ccaatttaat     180
gccagtacag gagttttag taaagatgtc tacgaatatt acgatccaac ttatttaaaa     240
accgatgctg aaaaagataa attttaaaa acaatgatta aattatttaa tagaattaat     300
tcaaaaccat caggacagag attactggat atgatagtag atgctatacc ttatcttgga     360
aatgcatcta caccgcccga caatttgca gcaaatgttg caaatgtatc tattaataaa     420
aaaattatcc aacctggagc tgaagatcaa ataaaaggtt aatgacaaa tttaataata     480
tttggaccag gaccagttct aagtgataat tttactgata gtatgattat gaatggccat     540
tccccaatat cagaaggatt tggtgcaaga atgatgataa gattttgtcc tagttgttta     600
aatgtattta taatgttca ggaaaataaa gatacatcta tatttagtag acgcgcgtat     660
tttgcagatc cagctctaac gttaatgcat gaactatac atgtgttaca tggattatat     720
ggaattaaga taagtaattt accaattact ccaaatacaa agaattttt catgcaacat     780
agcgatcctg tacaagcaga agaactatat acattcggag acatgatcc tagtgtata     840
agtccttcta cggatatgaa tatttataat aaagcgttac aaaatttca agatatagct     900
aataggctta atattgtttc aagtgcccaa gggagtggaa ttgatatttc cttatataaa     960
caaatatata aaaataaata tgattttgtt gaagatccta atggaaaata tagtgtagat    1020
aaggataagt ttgataaatt atataaggcc ttaatgtttg ctttactga aactaatcta    1080
gctggtgaat atggaataaa aactaggtat tcttatttta gtgaatattt gccaccgata    1140
aaaactgaaa aattgttaga caatacaatt tatactcaaa atgaaggctt taacatagct    1200
agtaaaaatc tcaaaacgga atttaatggt cagaataagg cggtaaataa agaggcttat    1260
gaagaaatca gcctagaaca tctcgttata tatagaatag caatgtgcaa gcctgtaatg    1320
tacaaaaata ccggtaaatc tgaacagtgt attattgtta ataatgagga tttattttc    1380
atagctaata agatagtttt ttcaaaagat ttagctaaag cagaaactat agcatataat    1440
acacaaaata atactataga aaataatttt tctatagatc agttgatttt agataatgat    1500
```

```
ttaagcagtg gcatagactt accaaatgaa aacacagaac catttacaaa ttttgacgac   1560
atagatatcc ctgtgtatat taaacaatct gctttaaaaa aaattttttgt ggatggagat   1620 agccttttg  aatatttaca tgctcaaaca tttccttcta atatagaaaa tctacaacta   1680
acgaattcat taaatgatgc tttaagaaat aataataaag tctatacttt tttttctaca   1740
aaccttgttg aaaaagctaa tacagttgta ggtgcttcac ttttttgtaaa ctgggtaaaa   1800 ggagtaaatag atgattttac atctgaatcc acacaaaaaa gtactataga taaagtttca   1860
gatgtatcca taattattcc ctatatagga cctgctttga atgtaggaaa tgaaacagct   1920
aaagaaaatt ttaaaaatgc ttttgaaata ggtggagccg ctatcttaat ggagtttatt   1980
ccagaactta ttgtacctat agttggatttt tttacattag aatcatatgt aggaaataaa   2040
gggcatatta ttatgacgat atccaatgct ttaagaaaaa gggatcaaaa atggacagat   2100
atgtatggtt tgatagtatc gcagtggctc tcaacggtta atactcaatt ttatacaata   2160
aaagaaagaa tgtacaatgc tttaaataat caatcacaag caatagaaaa aataatagaa   2220
gatcaatata atagatatag tgaagaagat aaaatgaata ttaacattga ttttaatgat   2280
atagatttta aacttaatca agtataaat ttagcaataa acaatataga tgattttata   2340
aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaaagtaa atagacacct aaaagacagt   2520
ataccatttg atcttcact  ataaccaag gacacaattt taatcaagt ttttaataat   2580 tatattagta atattagtag taatgctatt ttaagtttaa gttatagagg tgggcgttta   2640
atagattcat ctggatatgg tgcaactatg aatgtaggtt cagatgttat cttaatgat   2700 ataggaaatg gtcaatttaa attaaataat tctgaaaata gtaatattac ggcacatcaa   2760
agtaaattcg ttgtatatga tagtatgttt gataatttta gcattaactt tgggtaagg   2820 actcctaaat ataataataa tgatatacaa acttatcttc aaaatgagta tacaataatt   2880
agttgtataa aaaatgactc aggatggaaa gtatctatta agggaaatag aataatatgg   2940
acattaatag atgttaatgc aaaatctaaa tcaatatttt tcgaatatag tataaaagat   3000
aatatatcag attatataaa taaatggttt tccataacta ttactaatga tagattaggt   3060
aacgcaaata tttatataaa tggaagtttg aaaaaaagtg aaaaaatttt aaacttagat   3120
agaattaatt ctagtaatga tatagacttc aaattaatta attgtacaga tactactaaa   3180
tttgtttgga ttaaggattt taatattttt ggtagagaat taaatgctac agaagtatct   3240
tcactatatt ggattcaatc atctacaaat actttaaaag attttttgggg gaatccttta   3300 agatacgata cacaatacta tctgtttaat caaggtatgc aaaatatcta tataaagtat   3360
tttagtaaag cttctatggg ggaaactgca ccacgtacaa actttaataa tgcagcaata   3420
aattatcaaa atttatatct tggtttacga tttattataa aaaaagcatc aaattctcgg   3480
aatataaata atgataatat agtcagagaa ggagattata tatatcttaa tattgataat   3540
atttctgatg aatcttacag agtatatgtt ttggtgaatt ctaaagaaat tcaaactcaa   3600 ttattttag cacccataaa tgatgatcct acgttctatg atgtactaca aataaaaaaa   3660
tattatgaaa aaacaacata taattgtcag atactttgcg aaaaagatac taaaacattt   3720
gggctgtttg gaattggtaa atttgttaaa gattatggat atgtttggga tacctatgat   3780
```

```
aattattttt gcataagtca gtggtatctc agaagaatat ctgaaaatat aaataaatta   3840
aggttgggat gtaattggca attcattccc gtggatgaag gatggacaga ataa         3894

<210> SEQ ID NO 14
<211> LENGTH: 1297
<212> TYPE: PRT
<213> ORGANISM: Clostridium botulinum
<220> FEATURE:
<221> NAME/KEY: UNSURE
<222> LOCATION: (7)..(7)
<223> OTHER INFORMATION: Xaa can be any naturally occurring amino acid

<400> SEQUENCE: 14

Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335
```

```
Tyr Ser Val Asp Lys Asp Lys Phe Asp Lys Leu Tyr Lys Ala Leu Met
            340                 345                 350
Phe Gly Phe Thr Glu Thr Asn Leu Ala Gly Glu Tyr Gly Ile Lys Thr
            355                 360                 365
Arg Tyr Ser Tyr Phe Ser Glu Tyr Leu Pro Pro Ile Lys Thr Glu Lys
            370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
                435                 440                 445
Gln Cys Ile Ile Val Asn Asn Glu Asp Leu Phe Phe Ile Ala Asn Lys
                450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
                515                 520                 525
Gln Ser Ala Leu Lys Lys Ile Phe Val Asp Gly Asp Ser Leu Phe Glu
                530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
                595                 600                 605
Glu Ser Thr Gln Lys Ser Thr Ile Asp Lys Val Ser Asp Val Ser Ile
                610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
                675                 680                 685
Asn Ala Leu Lys Lys Arg Asp Gln Lys Trp Thr Asp Met Tyr Gly Leu
                690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
                740                 745                 750
```

```
Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn
    1010                1015                1020

Ile Tyr Ile Asn Gly Ser Leu Lys Lys Ser Glu Lys Ile Leu Asn
    1025                1030                1035

Leu Asp Arg Ile Asn Ser Ser Asn Asp Ile Asp Phe Lys Leu Ile
    1040                1045                1050

Asn Cys Thr Asp Thr Thr Lys Phe Val Trp Ile Lys Asp Phe Asn
    1055                1060                1065

Ile Phe Gly Arg Glu Leu Asn Ala Thr Glu Val Ser Ser Leu Tyr
    1070                1075                1080

Trp Ile Gln Ser Ser Thr Asn Thr Leu Lys Asp Phe Trp Gly Asn
    1085                1090                1095

Pro Leu Arg Tyr Asp Thr Gln Tyr Tyr Leu Phe Asn Gln Gly Met
    1100                1105                1110

Gln Asn Ile Tyr Ile Lys Tyr Phe Ser Lys Ala Ser Met Gly Glu
    1115                1120                1125

Thr Ala Pro Arg Thr Asn Phe Asn Asn Ala Ala Ile Asn Tyr Gln
    1130                1135                1140

Asn Leu Tyr Leu Gly Leu Arg Phe Ile Ile Lys Lys Ala Ser Asn
    1145                1150                1155
```

```
Ser Arg Asn Ile Asn Asn Asp Asn Ile Val Arg Glu Gly Asp Tyr
    1160            1165            1170

Ile Tyr Leu Asn Ile Asp Asn Ile Ser Asp Glu Ser Tyr Arg Val
    1175            1180            1185

Tyr Val Leu Val Asn Ser Lys Glu Ile Gln Thr Gln Leu Phe Leu
    1190            1195            1200

Ala Pro Ile Asn Asp Asp Pro Thr Phe Tyr Asp Val Leu Gln Ile
    1205            1210            1215

Lys Lys Tyr Tyr Glu Lys Thr Thr Tyr Asn Cys Gln Ile Leu Cys
    1220            1225            1230

Glu Lys Asp Thr Lys Thr Phe Gly Leu Phe Gly Ile Gly Lys Phe
    1235            1240            1245

Val Lys Asp Tyr Gly Tyr Val Trp Asp Thr Tyr Asp Asn Tyr Phe
    1250            1255            1260

Cys Ile Ser Gln Trp Tyr Leu Arg Arg Ile Ser Glu Asn Ile Asn
    1265            1270            1275

Lys Leu Arg Leu Gly Cys Asn Trp Gln Phe Ile Pro Val Asp Glu
    1280            1285            1290

Gly Trp Thr Glu
    1295
```

USE OF BOTULINUM NEUROTOXIN IN THE TREATMENT OF SIALORRHEA

CROSS-REFERENCE TO RELATED APPLICATIONS

This application is a continuation of U.S. patent application Ser. No. 16/129,311, filed Sep. 12, 2018, which claims priority under 35 U.S.C. § 365 as a continuation of International Application No. PCT/EP2018/056850, filed Mar. 19, 2018, which claims priority to European Patent Application No. 17162719.3, filed Mar. 24, 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000034-005001_Sequence_Listing_ST25.txt" created on Jun. 4, 2020, and 114,260 bytes in size) is submitted concurrently with the instant application, and the entire contents of the Sequence Listing are incorporated herein by reference.

BACKGROUND

This invention relates to improved uses of botulinum neurotoxins in the treatment of a disease or condition associated with sialorrhea or increased saliva production. In particular are botulinum neurotoxins disclosed which are administered into parotid and submandibular glands in a dose ratio between 1.45 to 1 and 1.7 to 1.

BACKGROUND OF THE INVENTION

Drooling is generally represented by a wide variety of clinical conditions which result in the symptom of saliva overflowing the lip margin (known as anterior drooling) or inadvertently overflowing the pharynx, involuntarily entering the glottis and the trachea (known as posterior drooling). As anterior drooling is mainly a problem for patients with regard to social interaction, posterior drooling can also cause cough and irritation in subjects with intact cough reflex or aspired silently in unconscious subjects.

The term drooling is often used in lay language for the medical term sialorrhea, hypersalivation or ptyalism depending on clinical condition, country of usage, specialty of medicine. Per definition, sialorrhea is the "excess spillage of saliva over the lip margin", hypersalivation is the "excessive production of saliva", ptyalism is the "hypersalivation in pregnant women". Those terms and definitions are not consistently used with respect to their unclear cause, and pathomechanism of the underlying conditions and problems.

Causes of sialorrhea can be various and generally relate to an overproduction of saliva or underperformance of saliva managing or eliminating anatomical structures or physiological functions. Of course the combination of those factors makes a clear distinction of causes impossible, therefore the descriptors like diagnoses of the symptoms as listed above are used contradictory. In some cases only anatomical malformations and deformities of salivary glands and ducts, lips, oral cavity, and teeth (defects in lip closure, dental malocclusion) causes local bypasses between the oral cavity and the external world enabling the uncontrolled outflow of the produced saliva.

Malformations, strictures, scars, fistulas and bypasses can occur as permanent consequences of oral or head and neck cancer, injuries and as complications of their surgery. Patients with intellectual disabilities may have permanently open mouth, causing the same effect with or without malformations. Reduced sensorimotor abilities, inefficient oral neuromuscular control, reduced protective reflexes, hypomotility of swallowing muscles, decreased swallowing frequency or ineffective swallowing or dysphagia appear to be the most frequent causes of inherent sialorrhea in patients with neurological conditions selected for example from Parkinson's disease, Progressive Supranuclear Palsy, Corticobasal Degeneration, Multiple System Atrophy, Amyotrophic lateral sclerosis (ALS), cerebral palsy, stroke, traumatic brain injury (TBI), clozapine induced hypersalivation, Rett syndrome, Angelman syndrome, epileptic encephalopathy and brain tumours, total pharyngolaryngectomy, supracricoid laryngectomy and supraglottic laryngectomy, dementia, or intellectual disability or any other cause of sialorrhea or hypersalivation. If not frequently swallowed down due to disturbed movement control of swallowing, the produced unstimulated or stimulated saliva is pooled in the oral cavity. Uncontrolled opening of mouth and anterograde posture of the head facilitates the overflowing of the pooled saliva over the lip margin of the patient.

Salivation can also be increased permanently by irritating factors e.g. massive caries or odontolith, hypertrophy of salivary glands, gastroesophageal reflux or by drugs or toxins inducing hypersalivation as a side effect (e.g. Clozapine, Benzodiazepines, Antipsychotics), causing permanent activation of salivary nuclei or nerve endings in the salivary glands.

Overproduction of saliva can only be controlled in otherwise healthy individuals to a certain extent. In patients with disabled saliva management the upper threshold of the ability to control pooled saliva in the mouth or to swallow the overproduced amount of saliva are lower, therefore more challenging.

Treatment options for swallowing problems focus on rehabilitative measures (swallowing training, oral motor control training) however the unconscious mechanisms of frequent swallowing can hardly be trained and developed in patients with progressive neurological diseases such as Parkinson's disease or ALS. Therefore treatment of sialorrhea is often focused on the reduction of saliva production. Earliest approaches used well-known anticholinergic drugs (e.g. Atropine, Ipratropium Bromide, Scopolamine, Glycopyrrolate, Tropicamide), acting inhibitory on muscarinic cholinergic nerves, which control the amount of produced saliva by salivary glands in and around the oral cavity. Several other derivatives of anticholinergics were also tested and used off label in this indication. Only Glycopyrrolate is approved for the treatment of drooling in children in the USA and EU recently.

Another treatment alternative is botulinum toxin, which is administered to patients by intramuscular injections to reduce muscle tonus and spasticity in treated muscles, or hyperhidrosis. Dry mouth was detected as adverse drug reaction in such patients and this motivated physicians to treat salivary glands with Botulinum toxin A or B directly i.e. by intraglandular or intraparenchymal injections of Botulinum toxin A or B into the major salivary glands parotids and submandibular glands.

*Clostridium* is a genus of anaerobe gram-positive bacteria, belonging to the Firmicutes. *Clostridium* consists of around 100 species that include common free-living bacteria as well as important pathogens, such as *Clostridium botu-*

*linum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterised by paralysis of various muscles. Paralysis of the breathing muscles can cause death of the affected individual.

Although both botulinum neurotoxin (BoNT) and tetanus neurotoxin (TeNT) function via a similar initial physiological mechanism of action, inhibiting neurotransmitter release from the axon of the affected neuron into the synapse, they differ in their clinical response. While the botulinum neurotoxin acts at the neuromuscular junction and other cholinergic synapses in the peripheral nervous system, inhibiting the release of the neurotransmitter acetylcholine and thereby causing flaccid paralysis, the tetanus neurotoxin, which is transcytosed into central neurons, acts mainly in the central nervous system, preventing the release of the inhibitory neurotransmitters GABA (gamma-am inobutyric acid) and glycine by degrading the protein synaptobrevin. The consequent overactivity of spinal cord motor neurons causes generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic serotypes, termed BoNT/A through BoNT/H with further subtypes. Most *Clostridium botulinum* strains produce one type of neurotoxin, but strains producing multiple neurotoxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial neurotoxins, is located between the two cysteine residues forming the disulfide bond. This loop region is proteolytically cleaved by an unknown clostridial endoprotease to obtain the biologically active neurotoxin.

The molecular mechanism of intoxication by TeNT and BoNT appears to be similar as well: entry into the target neuron is mediated by binding of the C-terminal part of the heavy chain to a specific cell surface receptor; the neurotoxin is then taken up by receptor-mediated endocytosis. The low pH in the so formed endosome then triggers a conformational change in the clostridial neurotoxin which allows it to embed itself in the endosomal membrane and to translocate through the endosomal membrane into the cytoplasm, where the disulfide bond joining the heavy and the light chain is reduced. The light chain can then selectively cleave so called SNARE-proteins, which are essential for different steps of neurotransmitter release into the synaptic cleft, e.g. recognition, docking and fusion of neurotransmitter-containing vesicles with the plasma membrane. TeNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C1 cleaves the integral plasma membrane protein syntaxin and SNAP-25.

In *Clostridium botulinum*, the botulinum neurotoxin is formed as a protein complex comprising the neurotoxic component and non-toxic proteins. The accessory proteins embed the neurotoxic component thereby protecting it from degradation by digestive enzymes in the gastrointestinal tract without adding anything to the toxic effect. Thus, botulinum neurotoxins of most serotypes are orally toxic. Complexes with, for example, 450 kDa or with 900 kDa are obtainable from cultures of *Clostridium botulinum.*

In recent years, botulinum neurotoxins have been used as therapeutic agents, for example in the treatment of dystonias and spasms, and have additionally been used in cosmetic applications, such as the treatment of fine wrinkles. Preparations comprising botulinum neurotoxin complexes are commercially available, e.g. from Ipsen Ltd (Dysport®), Solstice Neurosciences LLC/US Worldmeds LLC (Myobloc®) or Allergan Inc. (Botox®). A high purity neurotoxic component of botulinum neurotoxin, free of any complexing proteins, is for example available from Merz Pharmaceuticals GmbH, Frankfurt (Xeomin®, Bocouture®).

There are a couple of reports in the prior art about the use of botulinum neurotoxin A and B in patients with sialorrhea caused by different underlying diseases. For example, Breheret et al. (Annales francaises d Óto-rhino-laryngologie et de Pathologie Cervico-faciale, volume 128, Issue 5, 2011, pages 266-271), Barbero et al. (J Neurol. 2015 December; 262(12):2662-7), Suskind et al. (Laryngoscope. 2002 January; 112(1):73-81), Porta et al. (J Neurol Neurosurg Psychiatry. 2001 April; 70(4):538-40.), Narayanaswami et al. (Parkinsonism Relat Disord. 2016 September; 30:73-7) and Castelnovo et al. (Movement Disorders 2013, Volume 28, Abstract Supplement) report the use of different toxins according to several different protocols with varying amounts of toxin administered to the salivary glands for treating sialorrhea in a variety of medical conditions. Despite the number of studies providing data about safety and efficacy of using botulinum neurotoxins in sialorrhea, there are still a lot of ongoing discussions without clear recommendations about the dosages, the sites of administration and the type of toxin to be used.

BRIEF SUMMARY

One of the objects of the present invention is to provide a botulinum neurotoxin for treatment of a disease or condition associated with sialorrhea or increased saliva production which limits the activity of the salivary glands for a long period of time with an extent that the subject shows no drooling but which still allows that the reduced amount of produced saliva is sufficient for normal physiologic functioning, e.g. as lubricant, as ion reservoir, as buffer, as cleansing, for antimicrobial actions, for agglutination, for pellicle formation, for digestion, for taste, for excretion and/or for water balance. Another object of the present invention is to avoid side effects related to the treatment with a botulinum neurotoxin or to reduce them at least in frequency, severity and/or duration while under treatment. As a further object of the present invention, the botulinum neurotoxins should provide advantageous treatment results over a long period of treatment as the underlying disease will not be affected by the treatment, therefore long lasting therapy should be applicable effective and safe without waning of efficacy or compromising safety with repeated injection cycles for prolonged treatment.

Surprisingly, it has been identified that a botulinum neurotoxin can address one or more of these objections, if it is used in treating a disease or condition associated with sialorrhea or increased saliva production, wherein said botulinum neurotoxin is administered by injection into parotid glands and submandibular glands and wherein the ratio between the doses of botulinum neurotoxin administered to each of the parotid glands and each of the submandibular glands is between 1.45 to 1 and 1.7 to 1.

BRIEF DESCRIPTION OF THE SEVERAL VIEWS OF THE DRAWINGS

FIG. 1 shows mean reduction in objectively measured unstimulated salivary flow rate (uSFR) from baseline (FAS).

FIG. 2 shows mean global impression of change scale (GICS) (FAS). Superiority of NT 201 over placebo is shown by mean Global Impression of Change Scale (GICS) [FAS].

FIG. 3 shows response rate in subject's GICS over time (FAS).

FIG. 4 shows mean reduction of drooling severity and frequency sum score (DSFS) from baseline (FAS). Superiority of NT 201 over placebo is shown by the mean reduction of drooling severity and frequency sum score (DSFS) from baseline [FAS].

FIG. 5 shows mean mROMP drooling subscore reduction from baseline (FAS).

DETAILED DESCRIPTION OF THE INVENTION

The present invention may be understood more readily by reference to the following detailed description of the invention and the examples included therein.

In a first embodiment the present invention relates to a botulinum neurotoxin for use in treating a disease or condition associated with sialorrhea or increased saliva production, wherein said botulinum neurotoxin is administered by injection into parotid glands and submandibular glands and wherein the ratio between the doses of botulinum neurotoxin administered to each of the parotid glands and each of the submandibular glands is between 1.45 to 1 and 1.7 to 1. In a preferred embodiment the botulinum neurotoxin of the present invention is administered into parotid glands and submandibular glands wherein the ratio between the doses of botulinum neurotoxin administered to each of the parotid glands and each of the submandibular glands is between 1.50 to 1 and 1.6 to 1. In a particular preferred embodiment the botulinum neurotoxin of the present invention is administered into parotid glands and submandibular glands wherein the ratio between the doses of botulinum neurotoxin administered to each of the parotid glands and each of the submandibular glands is 1.50 to 1.

In a further embodiment the present invention relates to a method of treating a disease or condition associated with sialorrhea or increased saliva production in a patient, the method comprising administering a therapeutically effective amount of a botulinum neurotoxin by injection into parotid glands and submandibular glands, wherein the ratio between the doses of botulinum neurotoxin administered to each of the parotid glands and each of the submandibular glands is between 1.45 to 1 and 1.7 to 1. In a preferred embodiment the method of the present invention comprises administering a therapeutically effective amount of a botulinum neurotoxin by injection into parotid glands and submandibular glands, wherein the ratio between the doses of botulinum neurotoxin administered to each of the parotid glands and each of the submandibular glands is between 1.50 to 1 and 1.6 to 1. In a particular preferred embodiment the method of the present invention comprises administering a therapeutically effective amount of a botulinum neurotoxin by injection into parotid glands and submandibular glands, wherein the ratio between the doses of botulinum neurotoxin administered to each of the parotid glands and each of the submandibular glands is 1.50 to 1.

In a further aspect the present invention generally relates to botulinum toxins, for treating a disease or condition associated with sialorrhea or increased saliva production. In particular embodiments of the present invention the disease or condition associated with sialorrhea or increased saliva production is associated for example with Parkinson's disease, Progressive Supranuclear Palsy, Corticobasal Degeneration, Multiple System Atrophy, Amyotrophic lateral sclerosis (ALS), cerebral palsy, stroke, traumatic brain injury (TBI), clozapine induced hypersalivation, Rett syndrome, Angelman syndrome, epileptic encephalopathy, brain tumours, total pharyngolaryngectomy, supracricoid laryngectomy and supraglottic laryngectomy, dementia, or intellectual disability (e.g. global developmental delay, severe learning disability) or any other cause of sialorrhea or hypersalivation. A disease or condition associated with sialorrhea or increased saliva production according to the present invention can be also Down's syndrome, Smith-Lemli-Opitz syndrome, Möbius syndrome, MEGDEL syndrome, Beckwith-Wiedemann syndrome, lymphatic malformation of the tongue, Foix-Chavany-Marie syndrome, chromosomal abnormalities and genetic diseases like 17q21 deletion, familial dysautonomia, partial trisomy 22, Aicardi syndrome, SMA Type 1, GM1 gangliosidosis or Apert syndrome, Wilson disease, congenital brain malformation like hydrocephalus, microcephaly, pontocerebellar hypoplasia, posterior fossa mass, neuronal ceroid lipofuscinosis, Batten disease, metachromatic leukodystrophy, multiplex arthrogryposis, encephalopathy, lissencephaly or pachigyria, brain injuries like spinal cord injury, hypoxic ischemic encephalopathy, congenital toxoplasmosis, congenital CMV infection, post meningoencephalitis or post herpes encephalitis, neuromotor disorders like oral dyspraxia, suprabulbar palsy, operculum syndrome, myopathy, infantile spasms, myotonic dystrophy, Duchenne muscular dystrophy, Neurofibromatosis type I or mitochondriopathy, fetal alcohol syndrome, autism or juvenile Guillain-Barré Syndrome.

In particular embodiments of the present invention the disease or condition associated with sialorrhea or increased saliva production is associated with stroke, in particular the disease or condition associated with sialorrhea or increased saliva production occurred after stroke (post stroke).

In preferred embodiments of the present invention the disease or condition associated with sialorrhea or increased saliva production is associated for example with traumatic brain injury (TBI), post stroke, Parkinson's disease or atypical parkinsonism (Progressive Supranuclear Palsy [PSP], Multisystem Atrophy [MSA], Corticobasal Degeneration [CBD]). In another preferred embodiment of the present invention the disease or condition associated with sialorrhea or increased saliva production is traumatic brain injury (TBI), post stoke, Parkinson's disease or atypical parkinsonism (Progressive Supranuclear Palsy [PSP], Multisystem Atrophy [MSA], Corticobasal Degeneration [CBD]) with chronic sialorrhea for at least 3 months duration and sialorrhea severity of at least 2 score points on the Drooling Severity Subscale and a frequency of at least 2 score points on the Drooling Frequency Subscale and at least 6 score points on the sum score Drooling Severity and Frequency Scale. In another preferred embodiment of the present invention the disease or condition associated with sialorrhea or increased saliva production is traumatic brain injury (TBI), post stoke, Parkinson's disease or atypical parkinsonism (Progressive Supranuclear Palsy PSP, Multisystem Atrophy MSA, Corticobasal Degeneration CBD) with chronic sialorrhea having at least 0.3 g/min unstimulated salivary flow rate.

The present invention relates in a further embodiment to a pharmaceutical composition comprising a botulinum neurotoxin for the use in treating a disease or condition associated with sialorrhea or increased saliva production, and a pharmaceutical acceptable carrier, wherein said botulinum neurotoxin is administered by injection into parotid glands and submandibular glands and wherein the ratio between the doses of botulinum neurotoxin administered to each of the parotid glands and each of the submandibular glands is between 1.45 to 1 and 1.7 to 1.

According to one embodiment of the present invention the botulinum neurotoxin is administered into parotid glands and submandibular glands in a total dose between 70 U and 110 U. In a preferred embodiment the total dose of botulinum neurotoxin administered into parotid and submandibular glands is between 75 U and 100 U.

According to one embodiment of the present invention the botulinum neurotoxin is administered into parotid glands and submandibular glands in a total dose of 75 U. In an alternative embodiment the total dose of botulinum neurotoxin administered into parotid and submandibular glands is 100 U.

Generally, the botulinum neurotoxin can be administered according to the present invention into parotid glands and submandibular glands in a total dose between 0.5 and 2.35 U/Kg body weight. In a particular preferred embodiment the botulinum neurotoxin is administered into parotid glands and submandibular glands in a total dose between 1 and 1.25 U/Kg body weight. Due to the low body weight botulinum toxin is generally administered in children as displayed in the dosing table 8. In another embodiment total dosage of up to 2.5 U/kg are administered into parotid and submandibular gland in children.

According to a further aspect of the present invention, the botulinum neurotoxin is administered in an aqueous composition having a botulinum neurotoxin concentration in the range between 45 and 55 U/mL. In a preferred embodiment of the present invention the botulinum neurotoxin is administered as aqueous composition having a botulinum neurotoxin concentration of 50 U/mL. In a particular preferred embodiment the contents of a 100 U vial will be reconstituted with a total of 2.0 mL physiological saline and the volumes administered to parotid and submandibular glands are:

Parotid gland: 0.6 ml on each side,
Submandibular gland: 0.4 ml on each side.

If several consecutive treatment cycles are envisaged the injection volumes can be reduced if dry mouth or dysphagia occurs at previous treatment cycles. This reduction is recommended at the discretion of the injector to avoid further occurrence of such side effects. If the administration of reduced botulinum neurotoxin quantities is envisaged, the injection volumes administered to parotid and submandibular glands are:

Parotid gland: 0.45 ml on each side,
Submandibular gland: 0.3 ml on each side.

The biological activity is commonly expressed in Mouse Units (U). As used herein, 1 U is the amount of neurotoxic component of the botulinum neurotoxin, which kills 50% of a specified mouse population after intraperitoneal injection, i.e. the mouse i.p. LD50. Another particular useful method for determining the biological activity of a botulinum neurotoxin is a cell-based assay as it is disclosed for example in WO2009/114748, WO 2013/049508 or WO 2014/207109. The activity results obtained with such cell-based assays correspond to the activity values obtained in the mouse i.p. LD50 assay. Activity results obtained for Botulinum serotype A formulations like commercially available Incobotulinumtoxin A (Botulinumtoxin serotype A, without complexing proteins, Xeomin®, Merz Pharmaceuticals GmbH)) or Onabotulinumtoxin A (Botulinumtoxin serotype A, with complexing proteins, Botox®, Allergan Inc.) can be converted to values for other toxins using conversion rates known to the person skilled in the art. For example, the necessary dose of AbobotulinumtoxinA A (Botulinumtoxin serotype A, with complexing proteins, Dysport®, Ipsen Biopharm Limited) can be determined by multiplication of the dose of Incobotulinumtoxin A or Onabotulinumtoxin A with a factor of 2.5 to 5. The dose for RimabotulinumtoxinB (Botulinumtoxin serotype B, Myobloc®, Solstice Neurosciences/US WorldMeds LLC) can be calculated by multiplication of the dose of Incobotulinumtoxin A or Onabotulinumtoxin A with a factor of 20 to 40.

In a further embodiment of the present invention the botulinum neurotoxin is administered in a volume of between 0.3 and 0.5 mL per injection site into the submandibular glands and in a volume of between 0.5 to 0.7 mL per injection site into the parotid glands. In a particular preferred embodiment of the present invention the botulinum neurotoxin is administered in a volume of 0.4 mL per injection site into the submandibular glands and in a volume of 0.6 mL per injection site into the parotid glands.

In a further embodiment of the present invention the botulinum neurotoxin is injected into one site of each submandibular gland on both sides of the patient. Injections are applied into the geometrically centrum of the glands, depending on the anatomical extent of the gland.

In another embodiment of the present invention the botulinum neurotoxin is injected into one site of each parotid gland on both sides of the patient. Injections are applied into the geometrical centrum of the glands, depending on the anatomical extent of the gland.

In a preferred embodiment the total dose of botulinum neurotoxin is injected into one site of each submandibular gland and into one site of each parotid gland.

One embodiment of the present invention relates to a botulinum neurotoxin for use in treating a disease or condition associated with sialorrhea or increased saliva production, wherein said botulinum neurotoxin is administered by injection into parotid glands and submandibular glands and wherein the ratio between the doses of botulinum neurotoxin administered into each of the parotid glands and each of the submandibular glands is between 1.45 to 1 and 1.7 to 1, wherein the disease or condition associated with sialorrhea or increased saliva production is associated with stroke and wherein a total dose of 100 U of the botulinum neurotoxin is injected into one site of each submandibular gland and into one site of each parotid gland.

One embodiment of the present invention relates to a botulinum neurotoxin for use in treating a disease or condition associated with sialorrhea or increased saliva production, wherein said botulinum neurotoxin is administered by injection into parotid glands and submandibular glands and wherein the ratio between the doses of botulinum neurotoxin administered into each of the parotid glands and each of the submandibular glands is 1.5 to 1, wherein the disease or condition associated with sialorrhea or increased saliva production is associated with stroke and wherein a total dose of 100 U of the botulinum neurotoxin is injected into one site of each submandibular gland and into one site of each parotid gland, in particular into the geometrical centrum of the gland, respectively.

In particular embodiments of the present invention the botulinum neurotoxin is injected into parotid glands and submandibular glands without using ultrasound guidance. In this case the target site within the gland is determined by using anatomical landmark orientation as it is well known for a person skilled in the art. The parotid gland is located inferior and anterior to the external acoustic meatus and lies posterior to the mandibular ramus and anterior to the mastoid process of the temporal bone. The gland is roughly wedge shaped when seen superficially and is also wedge shaped when seen on horizontal sections. The parotid gland can be easily palpated. To find palpable landmarks for the parotid gland one should palpate between the mandibular anterior ramus and the sternocleidomastoid muscle. Starting palpating anterior to each ear, moving to the cheek area, and then inferior to the angle of the mandible. Using the anatomic landmarks the superficial borders of the parotid gland are palpated and the botulinum neurotoxin is injected into the middle of the parotid gland. Injection can be given into the upper or lower halves of the main glandular body. A single injection point needs to be selected. The same procedure applies to the other side of the subject. The submandibular gland is located beneath the floor of the mouth below the mandibular arch next to the following anatomic structures. Lying superior to the digastric muscles, each submandibular gland is divided into superficial and deep lobes, which are separated by the mylohyoid muscle. The superficial lobe comprises most of the gland, with the mylohyoid muscle runs under it. The deep lobe is the smaller part. Although the submandibular gland is not always easily palpable, its anatomical position is well defined. The injection is given, albeit very rarely, parallel to the excretory duct. The submandibular gland will be injected by fixating the gland with two fingers in the position below the mandibula. The needle will be inserted from the upwards forwards in the direction of the mouth floor in 70-90 degree to the mandibula (Holsinger 2005, Anatomy, Function, and Evaluation of the Salivary Glands).

In other embodiments the botulinum neurotoxin is injected into parotid glands and submandibular glands using ultrasound guidance. A person skilled in the art is well aware of applying ultrasound imaging techniques to fully determine size and localization of the target area within the body of the gland. A high frequency linear transducer >7.5 MHz can be used, for example, to identify and visualize the gland [Howlett, High resolution ultrasound assessment of the parotid gland (2003) British Journal of Radiology 76, 271-277].

It is generally envisaged that the botulinum neurotoxin is injected into parotid glands and submandibular glands more than one time. In particular embodiments the botulinum neurotoxin according to the present invention is administered in consecutive treatment cycles. According to the present invention a treatment cycle is the time interval between two administrations of the botulinum neurotoxin, i.e. a treatment cycle consists of one administration of the botulinum neurotoxin and a follow-up period until the next botulinum neurotoxin injection is administered. The botulinum neurotoxin is preferably administered in at least 2, at least 3, at least 4, at least 5, at least 6, at least 7 or at least 8 treatment cycles. In one embodiment the botulinum neurotoxin is administered in 2 to 6 treatment cycles, in particular in 4 treatment cycles.

The time interval between two consecutive administrations of the botulinum neurotoxin into parotid glands and submandibular glands can vary between 10 and 20 weeks or between 12 and 20 weeks. In another embodiment the time interval between two consecutive administrations of the botulinum neurotoxin into parotid glands and submandibular glands can vary between 6 and 10 weeks. In a preferred embodiment the time interval between two consecutive administrations the botulinum neurotoxin into parotid glands and submandibular glands vary between 12 and 18 weeks, or between 14 and 18 weeks. In a most preferred embodiment the time interval is 15, 16 or 17 weeks, in particular 16 weeks.

In one embodiment of the invention the time interval remains the same between all consecutive administrations of the botulinum neurotoxin into parotid glands and submandibular glands.

In one embodiment of the present invention the botulinum neurotoxin is injected into parotid glands and submandibular glands in at least 4 consecutive treatment cycles, wherein the time interval between the consecutive administrations of the botulinum neurotoxin is 16 weeks.

Generally, there are several ways to determine the efficacy of a botulinum toxin for the treatment of a disease or condition associated with sialorrhea or increased saliva production known to the person skilled in the art. Measurements and scales for determining the efficacy of a botulinum toxin for the treatment of sialorrhea or a disease or condition associated with increased saliva production can be selected from e.g. determining unstimulated Salivary Flow Rate (uSFR), Mean Global Impression of Change Scale (GICS), Drooling Severity and Frequency Scale (DSFS), modified Radboud Oral Motor Inventory for Parkinson's Disease (mROMP), Modified Teacher's Drooling Scale (mTDS), Drooling Impact Scale (DIS), Drooling Quotient (DQ) Drooling Rating Scale (DRS) and/or UPDRS Drooling Scale.

In particular embodiments at least two of these measurements and scales can be combined for determining the efficacy of a botulinum toxin for the treatment of sialorrhea or a disease or condition associated with increased saliva production.

In one embodiment of the present invention the botulinum toxin for the treatment of sialorrhea or a disease or condition associated with increased saliva production is used in a patient having a baseline saliva production, i.e. unstimulated Salivary Flow Rate (uSFR) between 0.1-1.6 g/min. In a preferred embodiment the botulinum toxin for the treatment of sialorrhea or a disease or condition associated with increased saliva production is used in a patient having a baseline saliva production, i.e. unstimulated Salivary Flow Rate (uSFR) of more than 0.3 g/min. In another embodiment the botulinum toxin for the treatment of sialorrhea or a disease or condition associated with increased saliva production is used in a patient having at baseline a Drooling Severity and Frequency Scale (DSFS) Sum Score 6 and Severity Subscore 2 and Frequency Subscore 2. Generally the determination of the uSFR and DSFS scores is well known to a person skilled in the art. According to the present invention the uSFR is determined by the weight of collected saliva for 5 minutes using four absorptive swabs for collection. Collection of saliva is performed by placing adsorptive material into the oral cavity (e.g. four dental rolls, Salivette® or Salimetrics Oral Swabs®) for 5 minutes. The absorptive material adsorbs saliva from the closed oral cavity and weight gain of absorptive material due to the collected amount of saliva can be determined by measuring the weight of the absorptive material before and after placing it into the oral cavity. A repetition of the collection and measurement of the amount of produced saliva for 5 minutes after a pause of 30 minutes provides a second value. The average of both values guarantees the reliability of measurement results (by reducing intraindividual variability of measurements) (Jongerius P H, van Limbeek J, Rotteveel J J. Assessment of salivary flow rate: biologic variation and measure error. Laryngoscope. 2004; 114(10):1801-4).

In a further embodiment of the present invention the administration of 100 U botulinum neurotoxin reduces the uSFR by at least 25% compared to baseline within 4 weeks after administration. In a preferred embodiment the administration of 100 U botulinum neurotoxin reduces the uSFR by at least 30% (median) compared to baseline within 4 weeks after injection. In another embodiment of the present invention the administration of 100 U botulinum neurotoxin reduces the uSFR by at least 22% (median) compared to baseline within 8 weeks after administration. In a preferred embodiment the administration of 100 U botulinum neurotoxin reduces the uSFR by at least 28% (median) compared to baseline within 8 weeks after injection.

In a further embodiment of the present invention the administration of 100 U of the botulinum neurotoxin improves the Global Impression of Change Scale (GICS) score for drooling assessed by the patient by at least +0.90 score points on a 7 point Likert like scale compared to baseline drooling within 4 weeks after administration. In a preferred embodiment the administration of 100 U of the botulinum neurotoxin shows a Global Impression of Change Scale (GICS) improvement of at least +1.00 score points compared to baseline drooling within 4 weeks after injection. In another embodiment of the present invention the administration of 100 U of the botulinum neurotoxin improves drooling measured by a Global Impression of Change Scale (GICS) by at least +1.00 score points compared to baseline drooling within 8 weeks after administration. In a preferred embodiment the administration of 100 U of the botulinum neurotoxin improves drooling measured by the Global Impression of Change Scale (GICS) by at least +0.90 score points compared to baseline within 12 weeks after injection. The Global Impression of Change Scale (GICS) is determined by a Likert-like scale answering the question "Compared to how you were doing just before the last injection into your salivary gland, what is your overall impression of how you are functioning now as a result of this treatment?" with scale answers ranging from "−3 very much worse" to "+3 very much improved" (Likert, Rensis (1932). "A Technique for the Measurement of Attitudes". Archives of Psychology. 140: 1-55)).

In a further embodiment of the present invention the administration of 100 U of the botulinum neurotoxin reduces the mean Drooling Severity and Frequency Scale (DSFS) sum score by at least 0.90 score points compared to baseline within 4 weeks after administration. In a preferred embodiment the administration of 100 U of the botulinum neurotoxin reduces the mean Drooling Severity and Frequency Scale (DSFS) sum score by at least 1.20 score points compared to baseline within 4 weeks after injection. In another embodiment of the present invention the administration of 100 U of the botulinum neurotoxin reduces the mean Drooling Severity and Frequency Scale (DSFS) sum score by at least 1.50 score points compared to baseline within 8 weeks after administration. The Drooling Severity and Frequency Scale (DSFS) is determined by two subscales, a 4-point Likert scale for 'drooling frequency' and a 5-point Likert scale for 'drooling severity'. The DSFS is the sumscore of the two subscales. The evaluation refers to the time period, "over the past week". The highest possible score is 9 (Thomas-Stonell N, Greenberg J. Three treatment approaches and clinical factors in the reduction of drooling. Dysphagia. 1988; 3(2):73-8.).

Drooling Severity

| 1 | Dry (never drools) |
| 2 | Mild (only lips wet) |
| 3 | Moderate (wet on lips and chin) |
| 4 | Severe (drool extends to clothes wet) |
| 5 | Profuse (hands, tray and objects wet) |

Drooling Frequency

| 1 | Never |
| 2 | Occasionally (not every day) |
| 3 | Frequently (part of everyday) |
| 4 | Constantly |

In a further embodiment of the present invention the administration of 100 U of the botulinum neurotoxin reduces the mean modified Radboud Oral Motor Inventory for Parkinson's Disease (mROMP) Saliva Control Domain sum score by at least 3.50 score points compared to baseline within 4 weeks after administration. In a preferred embodiment the administration of 100 U of the botulinum neurotoxin reduces the mean modified Radboud Oral Motor Inventory for Parkinson's Disease (mROMP) Saliva Control Domain sum score by at least 4.60 score points compared to baseline within 4 weeks after injection. In another embodiment of the present invention the administration of 100 U of the botulinum neurotoxin reduces the modified Radboud Oral Motor Inventory for Parkinson's Disease (mROMP) Saliva Control Domain sum score by at least 5.5 score points compared to baseline within 8 weeks after administration. In a preferred embodiment the administration of 100 U of the botulinum neurotoxin reduces the modified Radboud Oral Motor Inventory for Parkinson's Disease (mROMP) Saliva Control Domain sum score by at least 6.50 score points compared to baseline within 8 weeks after injection. The modified Radboud Oral Motor Inventory for Parkinson's Disease (mROMP) is determined by original ROMP Inventory [Kalf 2011, Arch. Phys. Med. Rehabil.] which is a Dutch 23-item questionnaire of 5-point Likert scales in the domains speech, swallowing and saliva control. The ROMP was modified (mROMP) to implement small changes in wording resulting from patient interviews during linguistic validation into US English. The mROMP has now 24 items with clearly distinguishable response options and a recall period of the last 7 days.

In one aspect of the present invention the botulinum neurotoxin is a botulinum neurotoxin complex. Complexes with, for example, 450 kDa or with 900 kDa are obtainable from cultures of *Clostridium botulinum*. A *Clostridium botulinum* neurotoxin complex according to the present invention comprises the neurotoxic component and non-toxic proteins. The accessory proteins embed the neurotoxic component thereby protecting it from degradation by digestive enzymes in the gastrointestinal tract without adding anything to the toxic effect.

In another aspect of the present invention the botulinum neurotoxin is the neurotoxic component of a botulinum neurotoxin complex. Generally the neurotoxic component has a molecular weight of 150 kDa. The neurotoxic component is devoid of any other protein component of the *Clostridium botulinum* neurotoxin complex.

The botulinum neurotoxin according to the present invention is selected from the group of different serotypes including botulinum neurotoxin serotype A (BoNT/A), botulinum neurotoxin serotype B (BoNT/B), botulinum neurotoxin serotype C1 (BoNT/C1), botulinum neurotoxin serotype D (BoNT/D), botulinum neurotoxin serotype E (BoNT/E), botulinum neurotoxin serotype F (BoNT/F) or botulinum neurotoxin serotype G (BoNT/G). The botulinum neurotoxin and, in particular, its light chain and heavy chain are derivable from one of the antigenically different serotypes of botulinum neurotoxins indicated above. In an aspect, said light and heavy chain of the botulinum neurotoxin are the light and heavy chain of a botulinum neurotoxin selected from the group consisting of: BoNT/A, BoNT/B, BoNT/C1, BoNT/D, BoNT/E, BoNT/F, or BoNT/G. In another aspect, a polynucleotide encoding said botulinum neurotoxin of the present invention comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), or SEQ ID NO: 13 (BoNT/G). Moreover, encompassed is, in an aspect, a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), or SEQ ID NO: 14 (BoNT/G). Further encompassed is in an aspect of the means and methods of the present invention, a botulinum neurotoxin comprising or consisting of an amino acid sequence selected from the group consisting of: SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), and SEQ ID NO: 14 (BoNT/G).

In another aspect, the said polynucleotide encoding a botulinum neurotoxin of the present invention is a variant of the aforementioned polynucleotides comprising one or more nucleotide substitutions, deletions and/or additions which in still another aspect may result in a polypeptide having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the nucleic acid sequence as shown in any one of SEQ ID NOs: 1, 3, 5, 7, 9, 11 or 13 or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the amino acid sequence as shown in any one of SEQ ID NOs: 2, 4, 6, 8, 10, 12, or 14. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polynucleotides encodes a polypeptide retaining one or more and, in another aspect, all of the biological properties of the respective botulinum neurotoxin, i.e. the BoNT/A, BoNT/B, BoNT/C1, BoNT/D, BoNT/E, BoNT/F or BoNT/G. Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637) or a cell-based assay as described in WO2009/114748, WO2014/207109 or WO 2013/049508. The biological activity is commonly expressed in Mouse Units (U). As used herein, 1 U is the amount of neurotoxic component of the botulinum neurotoxin, which kills 50% of a specified mouse population after intraperitoneal injection, i.e. the mouse i.p. LD50. In a further aspect, the variant polynucleotides can encode botulinum neurotoxins having improved or altered biological properties, e.g., they may comprise cleavage sites which are improved for enzyme recognition or may be improved for receptor binding or any other property specified above. A particular useful method for determining the biological activity of a botulinum neurotoxin is a cell-based assay as it is disclosed for example in WO2009/114748, WO 2013/049508 or WO 2014/207109.

Without being bound to theory it is furthermore envisaged that in particular a formulation of a botulinum neurotoxin free of complexing proteins (incobotulinumtoxin A Xeomin®), i.e. the neurotoxic component of botulinum neurotoxin being devoid of any other protein component of the *Clostridium botulinum* neurotoxin complex, in comparison to other botulinum neurotoxins with complexing proteins (Onabotulinumtoxin A, Botox®, Abobotulinum-toxinA, Dysport®, RimabotulinumtoxinB, Myobloc® or others with complexing proteins), allows a clinically reversible, functional inactivation of the cholinergic neural transmission without disrupting the intracellular structure of the salivary glands and salivary ducts. The use of the neurotoxic component of botulinum neurotoxin being devoid of any other protein component of the *Clostridium botulinum* neurotoxin complex also does not cause any physical damage in acinar cells as described in resected submandibular salivary glands of children after Botulinum toxin injections [Mosseri 2016, Otolaryngology—Head and Neck Surgery].

Generally, the blockade of nerve terminals by botulinum neurotoxins is irreversible; the clinical effects, however, are temporary as new nerve terminals sprout giving rise to new connections. Complexing proteins are regarded as biologically inactive compounds for treatment and they are generally considered to play no role in the efficacy of botulinum neurotoxins used in intramuscular injections for the treatment of spasticity, dystonia, hyperhidrosis, headache, depression, urinary detrusor spasm or in aesthetic indications like glabellar frown lines or wrinkles.

Complexing proteins are remnants of Clostridial proteins, which originate from the bacteria *Clostridium botulinum*. Those proteins are produced together with the neurotoxic component of the botulinum neurotoxin protein complex and they play a fundamental role in protection of the toxin in aggressive environments (e.g. acidic conditions in the stomach) and they help the internalization of the toxin through the epithelial barrier of the intestines. Complexing proteins consist of hemagglutinins and non-hemagglutinins and are considered as non-toxic proteins of the botulinum toxin protein complex. Hemagglutinins (HA) were described to disrupt the intercellular epithelial barrier in intestines by directly binding E-cadherin [Fujinaga 2009, Toxicon[ ] [Sugawara et al 2010 *J. Cell Biol.* [ ], [Lee 2014, *Science* [ ]. In salivary glands secretory epithelium, intercalated ductal epithelium and striated ductal epithelium develop from ectodermal germ lines similar to the intestinal epithelium. Of particular interest in the tight junctions of the salivary glands are the members of cadherin family, which play a role in salivary gland development, tissue organization, and cell differentiation. Epithelial (E)-cadherin is the main cell-cell adhesion molecule in epithelial tissues and is regarded as a master organizer of the epithelial phenotype. [Davies 2006, Developmental Cell]. In early morphogenesis, E-cadherin and β-catenin are likely to participate in salivary gland remodelling, whereas during cytodifferentiation, they form stable cell-cell contacts and may collaborate with Rho GTPases in the establishment and maintenance of salivary cell polarity" [Baker 2010, *Journal of Biomedicine and Biotechnology*. The unique intercellular structures like E-cadherins play a fundamental role in polarization of epithelial cells in intestines and salivary glands as well. Interference of E-cadherins with the complexing proteins of Botulinum toxins therefore interferes with the normal biological activity of the salivary glands. Xu and Shan, for example, demonstrated that after BoNT/A Prosigne® Hengli® (Lanzhou Biochemical Co., Gansu, China administration (i.e. a botulinum neurotoxin with complexing proteins) into rat submandibular glands, Aquaporin (AQP5) on the glandular cell membrane is downregulated, which may be a secondary effect of denervation (Xu et al. 2015 Journal of Dental Research, Shan et al. 2013 International Journal of Oral Science).

For preparing a pharmaceutical preparation comprising a botulinum neurotoxin the neurotoxin can be formulated by various techniques dependent on the desired application purposes which are known in the art. For example, the (biologically active) botulinum neurotoxin can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pa. In an aspect, the pharmaceutical composition can be dissolved in a diluent, prior to administration. The diluent is also selected so as not to affect the biological activity of the botulinum neurotoxin product. Examples of such diluents are distilled water or physiological saline. In addition, the pharmaceutical composition or formulation may also include other carriers or non-toxic, non-therapeutic, non-immunogenic stabilizers and the like. Thus, the formulated botulinum neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. A suitable formulation for HSA-stabilized formulation comprising a botulinum neurotoxin according to the present invention is for example disclosed in U.S. Pat. No. 8,398,998 B2. The formulated botulinum neurotoxin product may be used for human or animal therapy of various diseases or disorders in a therapeutically effective dose or for cosmetic purposes.

EXAMPLES

General Procedure:

A clinical trial was conducted in which 4 consecutive injections were followed by a 16 week observation period each, i.e. 4 consecutive treatment cycles. At the end of each treatment cycle, subjects were examined for eligibility to enter the next cycle. The first treatment cycle (Main Period [MP]) was conducted at two different dose levels of NT 201 (i.e. botulinum toxin serotype A without complexing proteins, Incobotulinumtoxin A) (75 U and 100 U) compared to placebo. Subjects were randomized to the respective treatment with a ratio of 2:2:1 (75 U: 100 U: placebo). The Incobotulinumtoxin A was reconstituted in physiological saline in a concentration of 50 U/mL and the patients received 30 U toxin into each parotid gland and 20 U into each submandibular gland in the 100 U dose group and 22.5 U toxin into each parotid gland and 15 U into each submandibular gland in the 75 U dose group, respectively. In both dose groups the total dose allocated to each parotid and submandibular gland was injected into one site of the respective gland. The MP was followed by 3 consecutive treatment cycles of a dose-blinded extension period where subjects received either 75 U or 100 U NT 201 in the same way as in the MP. Subjects who received placebo during MP were randomized 1:1 to receive either 75 U or 100 U NT 201 during the extension period so the overall dose randomization ratio was 1:1. The results from the MP of the trial show that both the 75 U and 100 U doses reach treatment effects of clinical relevance. They are summarized below.

Example 1: Results of the Placebo Controlled Main Period (uSFR)

Overall, 184 subjects with chronic troublesome sialorrhea were treated during the MP of the study. The study had two co-primary efficacy endpoints. One of the co-primary efficacy endpoints was the change in the unstimulated salivary flow rate (uSFR) from baseline to week 4 (see Table 1 for mean changes over time). At all time points, the uSFR was meaningfully reduced in both NT 201 treatment groups with the effect being more pronounced in the NT 201 100 U dose group as presented in FIG. 1. At Week 4, statistically significant superiority over placebo was shown for the NT 201 100 U group (p=0.004). Mean uSFR values in the NT 201 75 U with p-values less than 0.05 (Table 1) were reached at Weeks 8 and 12 (p-values: 0.022 and 0.019, respectively). The treatment effects observed in both the NT 201 100 U and NT 201 75 U groups can be considered as clinically relevant.

TABLE 1

Mean uSFR [g/min] at baseline and mean uSFR changes from baseline over time (FAS)

| Time points | Placebo | NT 201 75 U | P-value MMRM* vs. Placebo | NT 201 100 U | P-value MMRM* vs. Placebo |
| --- | --- | --- | --- | --- | --- |
| Baseline | 0.38 | 0.42 | | 0.40 | |
| Week 4 | −0.03 | −0.07 | 0.542 | −0.12 | 0.004 |
| Week 8 | 0.00 | −0.09 | 0.022 | −0.13 | <0.001 |
| Week 12 | 0.00 | −0.11 | 0.019 | −0.11 | 0.004 |
| Week 16 | 0.01 | −0.06 | 0.180 | −0.11 | 0.002 | uSFR = unstimulated salivary flow rate [g/min], FAS = Full Analysis Set, U = Unit, MMRM = Mixed Model Repeated Measures
*MMRM uses treatment, country, gender, use of ultrasound and etiology as fixed factors and uSFR at baseline as covariate Example 2: Results of the Placebo Controlled Main Period (GICS)

The other co-primary efficacy endpoint was the improvement in global functional scale of subjects measured by the Global Impression of Change Scale (GICS) at Week 4. The GICS is a 7-point Likert scale completed by subjects answering the question "Compared to how you were doing just before the last injection into your salivary gland, what is your overall impression of how you are functioning now as a result of this treatment?" Both dose groups reached an improvement. A statistically significant difference in favor of the 100 U treatment group over the placebo was seen in Week 4 (p=0.002, Table 2, FIG. 2). The 75 U group showed numerically better results compared to placebo at Week 4, but the difference shortly missed statistical significance (p=0.055). Nevertheless, p-values of less than 0.05 were reached in both dose groups at Week 8 and Week 12 and at Week 16 in the 100 U dose group as presented in FIG. 2.

TABLE 2

Mean Subject's GICS values over time (FAS)

| Post baseline time point | Placebo | NT 201 75 U | P-value MMRM* vs. Placebo | NT 201 100 U | P-value MMRM* vs. Placebo |
| --- | --- | --- | --- | --- | --- |
| Week 1 (TC) | +0.47 | +0.54 | 0.689 | +0.76 | 0.065 |
| Week 2 (TC) | +0.63 | +0.72 | 0.626 | +0.91 | 0.096 |
| Week 4 | +0.47 | +0.84 | 0.055 | +1.04 | 0.002 |
| Week 8 | +0.26 | +0.89 | 0.002 | +1.13 | <0.001 |
| Week 12 | +0.36 | +0.79 | 0.035 | +1.00 | 0.001 |
| Week 16 | +0.20 | +0.34 | 0.531 | +0.72 | 0.011 |

GICS = Global Impression of Change Scale, FAS = Full Analysis Set, U = Unit, MMRM = Mixed Model Repeated Measures, TC = telephone call
*MMRM uses treatment, country, gender, use of ultrasound and etiology as fixed factors and DSFS sum score at baseline as covariate Example 3: Results of the Placebo Controlled Main Period (GICS)

The predefined response criterion for the GICS endpoint to be considered clinically meaningful improvement of drooling was at least one point improvement on the scale (minimally improved). Results of the responder analysis for all treatment groups are presented in Table 3 and FIG. 3.

TABLE 3

Response rate in Subject's GICS (FAS)

| Post baseline time point | Placebo | NT 201 75 U | P-value Fisher's exact test vs. placebo | NT 201 100 U | P-value Fisher's exact test vs. placebo |
| --- | --- | --- | --- | --- | --- |
| Week 1 (TC) | 36.1% | 51.4% | 0.157 | 59.5% | 0.026 |
| Week 2 (TC) | 48.6% | 62.2% | 0.215 | 66.2% | 0.095 |
| Week 4 | 44.4% | 64.4% | 0.064 | 72.6% | 0.006 |
| Week 8 | 28.6% | 68.1% | <0.001 | 76.4% | <0.001 |
| Week 12 | 38.9% | 58.6% | 0.066 | 70.8% | 0.002 |
| Week 16 | 40.0% | 41.2% | 1.000 | 59.7% | 0.065 |

FAS = full analysis set, U = units, TC = telephone call

The response rate of the placebo group was lower than those of both NT 201 treatment groups throughout the Main Period. It varied from 28.6% (at Week 8) to 48.6% at Week 2. In the two NT 201 groups, the maximal Subject's GICS response rate is reached at Week 8 with 68.1% in the NT 201 75 U group and 76.4% in the NT 201 100 U group. The inventors considers these rates as evidence of clinical meaningfulness of both the NT 201 75 U and 100 U dose groups.

Example 4: Results of the Placebo Controlled Main Period (DSFS)

The subjective endpoint Drooling Severity and Frequency Scale (DSFS) was also assessed. The DSFS consists of two sub-scales, a 4-point Likert scale for "drooling frequency" and a 5-point Likert scale for "drooling severity". Descriptive analyses of DSFS showed clinically relevant improvement of sialorrhea in both NT 201 treatment groups in comparison to no relevant improvement in the placebo group. Mean sum score changes from baseline over time are maximal with an improvement of −1.89 in the 100 U treatment group at Week 8 followed by −1.76 in the 75 U treatment group at Week 12 as presented in Table 4 and FIG. 4. Treatment comparison via Mixed Model Repeated Measures (MMRM) reveals p-values of <0.05 for both NT 201 groups when compared to placebo at Week 4, 8, and 12.

TABLE 4

Mean DSFS sum score at baseline and mean DSFS sum score changes from baseline over time (FAS)

| Time point | Placebo | NT 201 75 U | P-value MMRM* vs. Placebo | NT 201 100 U | P-value MMRM* vs. Placebo |
|---|---|---|---|---|---|
| Baseline | 6.97 | 6.88 | | 6.78 | |
| Week 4 | −0.53 | −1.35 | 0.002 | −1.55 | <0.001 |
| Week 8 | −0.71 | −1.60 | 0.002 | −1.89 | <0.001 |
| Week 12 | −1.03 | −1.76 | 0.008 | −1.54 | 0.030 |
| Week 16 | −0.77 | −1.07 | 0.223 | −1.10 | 0.116 |

*MMRM uses treatment, country, gender, use of ultrasound and etiology as fixed factors and DSFS sum score at baseline as covariate

Example 5: Results of the Placebo Controlled Main Period (mROMP)

Finally, the modified Radboud Oral Motor Inventory for Parkinson's disease (mROMP) was assessed using the drooling subscale that includes a 9-item questionnaire of 5-point Likert scales. Both NT 201 treatment groups showed superior efficacy results in mROMP drooling in comparison to the placebo group presented in Table 5 and FIG. 5. Mean changes from baseline over time reach a maximum improvement of −6.58 in the 100 U treatment group at Week 8 and −6.77 in the 75 U treatment group at Week 12. The inventors conclude that treatment effects seen in both dose groups were superior over the effect of placebo and NT 201 effects were consistent among all measures and robust throughout the observation to confirm appropriate clinical relevance of both doses.

TABLE 5

Change in mROMP drooling scores from study baseline to weeks 4, 8, 12 and 16-MP (FAS, OC)

| | Placebo (N = 36) | | NT 201 75 U (N = 74) | | NT 201 100 U (N = 74) | |
|---|---|---|---|---|---|---|
| | n obs | Mean (SD) | n obs | Mean (SD) | n obs | Mean (SD) |
| | Change from study baseline | | | | | |
| Week 4 | 36 | −1.00 (4.71) | 72 | −4.63 (5.26) | 73 | −5.66 (6.16) |
| Week 8 | 35 | −1.26 (4.91) | 72 | −6.29 (6.52) | 72 | −6.58 (5.90) |
| Week 12 | 35 | −1.77 (4.54) | 70 | −6.77 (6.05) | 72 | −6.40 (5.20) |
| Week 16 | 35 | −1.46 (5.03) | 68 | −4.44 (5.56) | 70 | −4.61 (5.40) |

Score ranges from 9 (best) to 45 (worst).

Example 6: Subgroup Analysis of Results of the Placebo Controlled Main Period (mROMP)

Subgroup analysis by etiology showed that subjects with sialorrhea after stroke in the NT 201 100 U group had higher mean decreases in uSFR than subjects with sialorrhea associated with Parkinson's disease or atypical parkinsonism (Table 6).

TABLE 6

Subgroup analysis of change in uSFR from study baseline to week 4-MP (Full Analysis Set FAS, Observed Cases OC)

| | Placebo | | NT 201 75 U | | NT 201 100 U | |
|---|---|---|---|---|---|---|
| | n obs | Mean (SD) | n obs | Mean (SD) | n obs | Mean (SD) |
| Etiology of sialorrhea | | | | | | |
| Sialorrhea associated with Parkinson's disease or atypical parkinsonism | 29 | −0.04 (0.23) | 58 | −0.08 (0.15) | 58 | −0.11 (0.19) |
| Sialorrhea after stroke | 6 | 0.04 (0.12) | 13 | −0.02 (0.14) | 13 | −0.20 (0.28) |
| Sialorrhea after TBI | 1 | −0.02 (—) | 2 | −0.07 (0.37) | 2 | −0.12 (0.10) | uSFR is given in g/min
DSFS sum score ranges from 2 (best) to 9 (worst).

Example 7: Efficacy in 3 Consecutive Treatment Cycles with 16 Weeks Intervals Efficacy results in 3 consecutive treatment cycles with 16 weeks intervals provided evidence for further improvement of sialorrhea. The change in uSFR from study baseline to all observation time points after the second injection, and the change from each injection (weeks 16, 32 and 48 after the first injection) to the respective assessment time points (weeks 20, 36 and 52 after the first injection), and to the end-of-cycle/end-of-study visits (weeks 32, 48 and 64 after the first injection) in each cycle was evaluated also.

Summary statistics for the uSFR at the cycle baselines of the extension period (EP) without placebo control group are displayed in Table 7. (Subjects randomized to the placebo group at the MP were randomized within the same setting to the 75 U or 100 U dose group in a 1:1 randomization ratio for the EP. Subjects in the 75 U or 100 U dose group in MP were maintained on their dose in the EP). The mean uSFR in the EP in both NT 201 treatment groups was highest at the cycle 2 baseline and lowest at the cycle 4 baseline. Additionally, the mean uSFR at each cycle baseline were slightly higher in the NT 201 75 U group than in the NT 201 100 U group. Similar improvement of sialorrhea was observed when GICS, DSFS and mROMP were analyzed for NT201 100 U and NT201 75 U over the extension period.

TABLE 7

Mean uSFR at all cycle baselines-EP (Safety Evaluation Set SES-EP, Observed Cases OC)

| | NT 201 75 U | | NT 201 100 U | |
| --- | --- | --- | --- | --- |
| | n obs | Mean (SD) | n obs | Mean (SD) |
| Cycle 2 Baseline | 83 | 0.38 (0.25) | 89 | 0.30 (0.18) |
| Cycle 3 Baseline | 79 | 0.31 (0.22) | 84 | 0.24 (0.17) |
| Cycle 4 Baseline | 79 | 0.28 (0.24) | 78 | 0.23 (0.16) | uSFR is given in g/min. Randomized treatment group was used.

TABLE 8

Dosing table for botulinum toxin administration into parotid and submandibular glands in children.

| | Parotid gland, each side | | Submandibular gland, each side | | | |
| --- | --- | --- | --- | --- | --- | --- |
| Body weight [kg] | Total dose per gland [units] | Volume per injection [ml] | Total dose per gland [units] | Volume per injection [ml] | Total dose (both sides) [units] | Total injection volume [ml] |
| ≥12 <15 | 6 | 0.24 | 4 | 0.16 | 20 | 0.8 |
| ≥15 <19 | 9 | 0.36 | 6 | 0.24 | 30 | 1.2 |
| ≥19 <23 | 12 | 0.48 | 8 | 0.32 | 40 | 1.6 |
| ≥23 <27 | 15 | 0.60 | 10 | 0.40 | 50 | 2.0 |
| ≥27 <30 | 18 | 0.72 | 12 | 0.48 | 60 | 2.4 |
| ≥30 | 22.5 | 0.90 | 15 | 0.60 | 75 | 3.0 |

The invention claimed is:

1. A method for treating a disease or condition associated with sialorrhea or increased saliva production in a patient, the method comprising administering a therapeutically effective amount of a botulinum neurotoxin by injection into the parotid glands and submandibular glands of the patient in at least four consecutive treatment cycles,
wherein the disease or condition is further associated with stroke, traumatic brain injury (TBI), clozapine induced hypersalivation, Rett syndrome, Angelman syndrome, epileptic encephalopathy, brain tumours, or intellectual disability,
wherein there is a time interval between the consecutive treatment cycles of between 14 and 18 weeks,
wherein each treatment cycle comprises administering the botulinum neurotoxin in a total dose between 1 and 2.5 U/Kg body weight, and the total dose of the botulinum neurotoxin administered into the parotid glands and submandibular glands is between 20 U and 75 U,
and wherein the ratio between the amount of the botulinum neurotoxin administered into each of the parotid glands and each of the submandibular glands is between 1.45 to 1 and 1.7 to 1.

2. The method according to claim 1, wherein said botulinum neurotoxin is injected into one site of each submandibular gland and/or into one site of each parotid gland.

3. The method according to claim 1, wherein the botulinum neurotoxin is injected into the parotid glands and submandibular glands using ultrasound guidance.

4. The method according to claim 1, wherein said botulinum neurotoxin is a botulinum neurotoxin complex.

5. The method according to claim 1, wherein said botulinum neurotoxin is the neurotoxic component of a botulinum neurotoxin complex, wherein said neurotoxic component is devoid of any other protein component of the *Clostridium botulinum* neurotoxin complex.

6. The method according to claim 1, wherein said botulinum neurotoxin is selected from the group of botulinum neurotoxin serotypes consisting of botulinum neurotoxin serotype A, botulinum neurotoxin serotype B, botulinum neurotoxin serotype C1, botulinum neurotoxin serotype D, botulinum neurotoxin serotype E, botulinum neurotoxin serotype F and botulinum neurotoxin serotype G.

7. The method according to claim 1, wherein the disease or condition is associated with stroke.

8. The method according to claim 1, wherein the time interval is between 15 and 17 weeks.

9. The method according to claim 1, wherein said botulinum neurotoxin is administered in an aqueous composition having a botulinum neurotoxin concentration of 25 U/mL.

10. The method according to claim 1, wherein said botulinum neurotoxin is administered in 0.16 to 0.60 ml per injection site into the submandibular glands and in 0.24 to 0.9 ml per injection site into the parotid glands.

11. The method according to claim 1, wherein the ratio between the amount of the botulinum neurotoxin administered into each of the parotid glands and each of the submandibular glands is between 1.5 to 1 and 1.6 to 1.

12. The method according to claim 1, wherein the ratio between the amount of the botulinum neurotoxin administered into each of the parotid glands and each of the submandibular glands is 1.5 to 1.

13. The method according to claim 1, wherein the time interval is 16 weeks.

14. The method according to claim 1, wherein each treatment cycle comprises administering the botulinum neurotoxin in a total dose between 1.3 and 2.2 U/Kg body weight.

15. The method according to claim 1, wherein the time interval is 15 weeks.

16. The method according to claim 1, wherein the time interval is 17 weeks.

17. The method according to claim 1, wherein the disease or condition is associated with traumatic brain injury (TBI).

18. The method according to claim 1, wherein the disease or condition is associated with clozapine induced hypersalivation.

19. The method according to claim 1, wherein the disease or condition is associated with Rett syndrome or Angelman syndrome.

20. The method according to claim 1, wherein the disease or condition is associated with epileptic encephalopathy.

21. The method according to claim 1, wherein the disease or condition is associated with brain tumours.

22. The method according to claim 1, wherein the disease or condition is associated with intellectual disability.

* * * * *